US009448184B1

(12) United States Patent
Liu et al.

(10) Patent No.: US 9,448,184 B1
(45) Date of Patent: *Sep. 20, 2016

(54) METHOD AND SYSTEM FOR DETERMINING ONE OR MORE OPTICAL CHARACTERISTICS OF STRUCTURE OF A SEMICONDUCTOR WAFER

(71) Applicant: KLA-Tencor Corporation, Milpitas, CA (US)

(72) Inventors: Xuefeng Liu, San Jose, CA (US); Yung-Ho Alex Chuang, Cupertino, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/180,923

(22) Filed: Feb. 14, 2014

Related U.S. Application Data

(63) Continuation of application No. 13/734,506, filed on Jan. 4, 2013, now Pat. No. 8,675,188.

(60) Provisional application No. 61/584,420, filed on Jan. 9, 2012.

(51) Int. Cl.
  *G01N 21/00* (2006.01)
  *G01J 4/00* (2006.01)
  *G01N 21/95* (2006.01)

(52) U.S. Cl.
  CPC .................. *G01N 21/9501* (2013.01)

(58) Field of Classification Search
  CPC ............. G01N 21/47; G01N 21/4788; G01N 21/9501; G01N 21/95607; H01L 22/12
  USPC .................. 356/237.1–237.5, 445–448, 369, 356/601–623; 702/40, 76, 108
  See application file for complete search history.

(56) References Cited

U.S. PATENT DOCUMENTS

| 4,999,014 A | 3/1991 | Gold et al. |
| 5,181,080 A | 1/1993 | Fanton et al. |

(Continued)

FOREIGN PATENT DOCUMENTS

| KR | 10-2010-008559 A | 7/2010 |
| KR | 10-2010-0085595 A | 7/2010 |

OTHER PUBLICATIONS

Katsumata et al., Pipe-shaped BiCS Flash Memory with 16 Stacked Layers and Multi-Level-Cell Operation for Ultra High Density Storage Devices, 2009 Symposium on VLSI Technology Digest of Technical Papers, pp. 136-137.

(Continued)

*Primary Examiner* — Hoa Pham
(74) *Attorney, Agent, or Firm* — Suiter Swantz pc llo

(57) ABSTRACT

Determination of one or more optical characteristics of a structure of a semiconductor wafer includes measuring one or more optical signals from one or more structures of a sample, determining a background optical field associated with a reference structure having a selected set of nominal characteristics based on the one or more structures, determining a correction optical field suitable for at least partially correcting the background field, wherein a difference between the measured one or more optical signals and a signal associated with a sum of the correction optical field and the background optical field is below a selected tolerance level, and extracting one or more characteristics associated with the one or more structures utilizing the correction optical field.

29 Claims, 16 Drawing Sheets

(56) References Cited

U.S. PATENT DOCUMENTS

| | | |
|---|---|---|
| 5,189,481 A | 2/1993 | Jann et al. |
| 5,440,674 A | 8/1995 | Park |
| 5,608,526 A | 3/1997 | Piwonka-Corle et al. |
| 5,963,329 A | 10/1999 | Conrad et al. |
| 6,201,601 B1 | 3/2001 | Vaez-Iravani et al. |
| 6,271,916 B1 | 8/2001 | Marxer et al. |
| 6,429,943 B1 | 8/2002 | Opsal et al. |
| 6,678,046 B2 | 1/2004 | Opsal |
| 6,804,635 B1 | 10/2004 | Dhondt |
| 7,031,848 B2 | 4/2006 | Opsal et al. |
| 7,038,850 B2 | 5/2006 | Chang et al. |
| 7,106,459 B2 | 9/2006 | Chu |
| 7,352,457 B2 | 4/2008 | Kvamme et al. |
| 7,525,649 B1 | 4/2009 | Leong et al. |
| 8,045,179 B1 | 10/2011 | Zhuang et al. |
| 8,468,471 B2 | 6/2013 | Liu et al. |
| 8,675,188 B2 * | 3/2014 | Liu et al. ............... 356/237.4 |
| 2003/0182013 A1 * | 9/2003 | Moreas et al. ............. 700/145 |
| 2007/0002465 A1 | 1/2007 | Chuang et al. |
| 2009/0002695 A1 * | 1/2009 | Saito et al. ............... 356/237.4 |
| 2010/0141948 A1 | 6/2010 | Cohen et al. |
| 2012/0323356 A1 | 12/2012 | Dziura et al. |

OTHER PUBLICATIONS

M.G. Moharam, Eric B. Grann, and Drew A. Pommet, Formulation for stable and efficient implementation of the rigorous coupled-wave analysis of binary gratings, J. Opt. Soc. Am., vol. 12, No. 5, May 1995, pp. 1068-1076, © 1995 Optical Society of America.

Philippe Lalanne, Improved formulation of the coupled-wave method for two-dimensional gratings, J. Opt. Soc. Am., vol. 14, No. 7, Jul. 1997, pp. 1592-1598, © 1997 Optical Society of America.

* cited by examiner

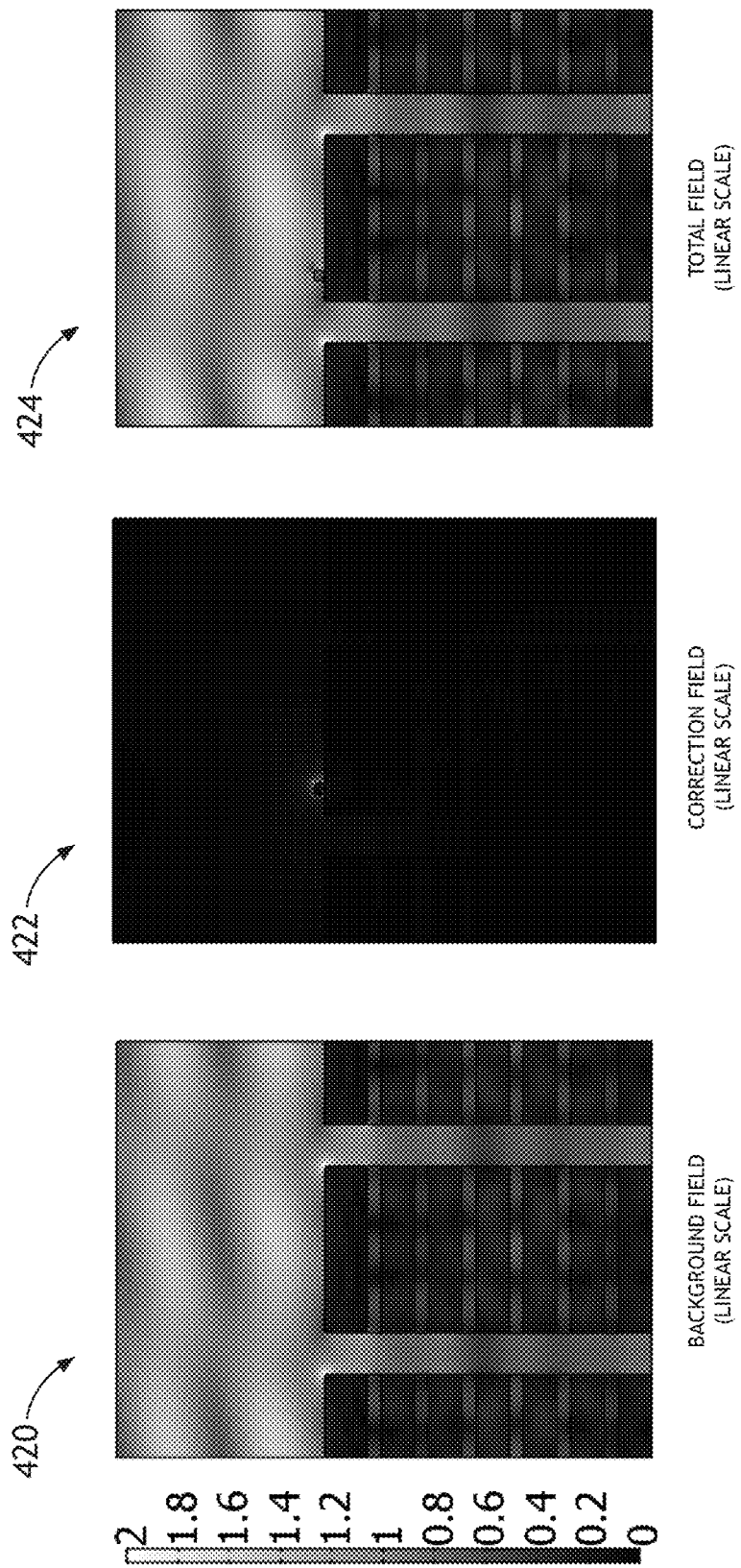

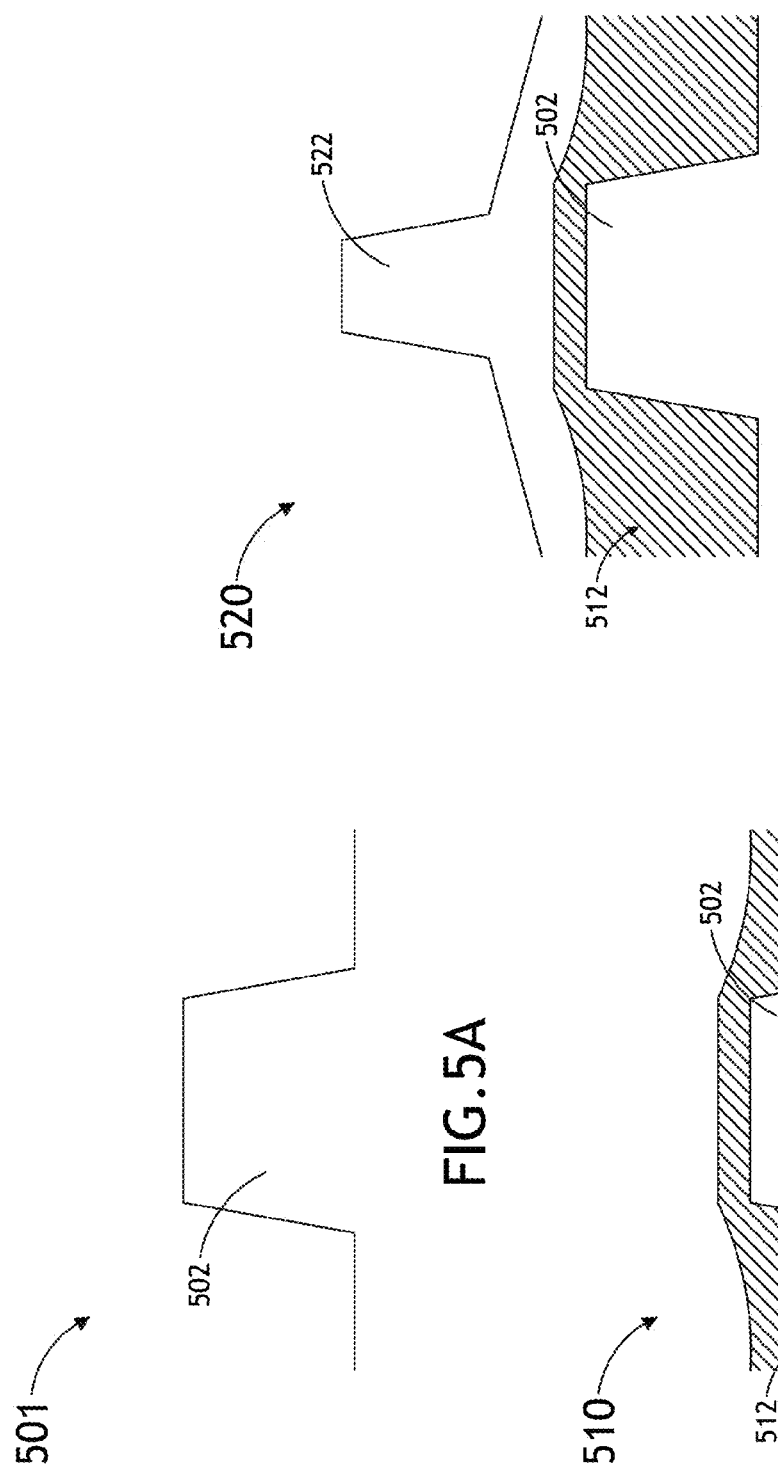

METHOD AND SYSTEM FOR DETERMINING ONE OR MORE OPTICAL CHARACTERISTICS OF STRUCTURE OF A SEMICONDUCTOR WAFER

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation of United States Patent Application entitled METHOD AND SYSTEM FOR DETERMINING ONE OR MORE OPTICAL CHARACTERISTICS OF STRUCTURE OF A SEMICONDUCTOR WAFER, naming Xuefeng Liu, Yung-Ho Alex Chuang, and John Fielden as inventors, filed Jan. 4, 2013, application Ser. No. 13/734,506, which is a regular (non-provisional) patent application of United States Provisional Patent Application entitled EFFICIENT COMPUTATION OF SCATTERING AND DIFFRACTION FROM COMPLEX STRUCTURES, naming Xuefeng Liu, Yung-Ho Alex Chuang, and John Fielden as inventors, filed Jan. 9, 2012 Application Ser. No. 61/584,420.

TECHNICAL FIELD

The present invention generally relates to the determination of optical characteristics of a structure of a semiconductor wafer and, in particular, to the determination of reflectivity, scattering, or diffraction of a structure of a semiconductor wafer.

BACKGROUND

Semiconductor metrology commonly requires measurement of periodic structures that are as large as or larger than the measurement spot of the measurement instrument. In some instances, these structures consist of test structures placed in the scribe line between dies of a semiconductor wafer. In other cases, these periodic structures are the structures forming the active circuits in the die (e.g., a memory array within a die). In yet other case, these periodic structures are small test structures placed within the die. In cases where the periodic structure substantially fills the measurement spot, it can generally be effectively modeled as an infinite structure.

During semiconductor wafer inspection, defects or particles commonly need to be detected on the device structures within the die. In many cases, these structures may be periodic or substantially periodic. For example, the structures may be periodic if they consist of a memory array, or if restrictive design rules require transistors to be laid out on a regular grid. In an inspection tool, a large area (such as a rectangle or line) may be illuminated simultaneously, whereby the illuminated area is then imaged onto a detector (e.g., CCD) such that different detector elements correspond to different locations within the illuminated area. If the image of a structure substantially fills one element of the detector and is substantially periodic, it may be sufficiently accurate to calculate its reflectivity by treating it as if it were an infinitely large periodic pattern.

The most commonly used method for calculating diffraction from a periodic structure on a semiconductor wafer is the rigorous coupled-wave analysis (RCWA), also referred to as the rigorous coupled-wave theory (RCWT). In general, RCWA computes diffraction by first dividing a given structure into a series of horizontal slabs. Then, within each slab, approximating the dielectric constant and the fields as finite sums of periodic functions of the horizontal position within the given slab. Commonly, the dielectric function (or the reciprocal of the dielectric function) is expressed as a finite Fourier series of position. Within each slab, the relationship between the fields at the top and bottom of the slab is calculated. Starting from the bottom, the relationships between fields at the top of one slab and the bottom of the next are computed, until the top of the structure is reached and the reflectivity of the structure as a whole can be computed given the specific illumination conditions.

Alternatively, other methods include those based on Green's functions and finite-difference time-domain (FDTD) methods. These methods are typically optimized for periodic structures when used in optical scatterometry metrology applications in the semiconductor industry.

However, when a finite sized structure or defect is combined with an effectively infinitely sized periodic structure, the resulting structure can no longer be regarded as an infinitely large periodic structure. Such situations are encountered commonly in the semiconductor industry. For example, a small metrology target may be placed on top of a large periodic pattern. The small target may be smaller than the measurement spot and so treating the structure as infinitely large may result in significant inaccuracies. Another common example includes settings where a defect exists within, on, or under a periodic pattern. In this setting, the defect may consist of extra material (e.g., a particle, bridge or oversized feature) or missing material (e.g., missing or undersized feature or a void). In this case, the structure is no longer periodic due to the extra or missing material that is present in only one unit cell and does not repeat (or is not at the same location) in other unit cells.

Traditionally, in order to approximately calculate the reflectivity, diffraction or scattering of such non-periodic structures using an algorithm, such as RCWA that assumes a periodic structure, it is necessary to construct a new larger unit cell containing multiple unit cells of the underlying structure. In the case of a small defect, only one of those unit cells actually contains the defect. In the case of a small target on top of a larger grating, the new unit cell must contain the entire small target. In order to obtain a reasonably accurate result the new unit cell should be large enough that the electric fields from the non-repeating feature have decayed to a relatively small value at the edge of the new periodic structure. For example, in the case of a small defect, this may require that the unit cell be a few (approximately 3-5) wavelengths in each dimension. By way of another example, in the case of the small metrology target, the new unit cell may need to be several times the size of the small target.

By way of example, in the case of the defect, the pitch of the original periodic structure might be less than 100 nm (e.g., 30-50 nm), in one direction in a dense memory array. If the longest illumination wavelength is approximately 300 nm, then the larger unit cell that includes the defect would need to be ten or more times larger than the period of the repeating structure. In the case of a 2D grating, the pitch in the other repeating direction would be even larger (e.g., 300-500 nm). As such, along that direction increasing the unit cell size two to three times may be sufficient. In this case, the example given the unit cell may require a size that is 10-30 times the size of the periodic structure. In order to resolve the same small features, the truncation order has to be increased by the same factor in each dimension as the unit cell increases the given dimension. Computation times for RCWA typically scale as the cube of the truncation order (for large truncation orders). As such, the computation time required to account for such a feature might increase by a factor of 1000 or more if the accuracy of the computation is to be maintained. Further, the memory requirements typically scale approximately as the square of the truncation order, requiring a factor of 100 times more memory for a ten-fold increase in the truncation order. Therefore, it would be desirable to provide a system and method that cures the defects of the prior.

SUMMARY

A system for determining one or more optical characteristics of a structure is disclosed. In one aspect, the system may include, but is not limited to, an optical measurement system configured to measure one or more optical signals from one or more structures of a sample; a computer control system communicatively coupled to the optical measurement system, the computer control system configured for: receiving one or more measured optical signals of the one or more structures from the optical measurement system; determining a background optical field associated with a reference structure having a selected set of nominal characteristics based on the one or more structures; determining a correction optical field suitable for at least partially correcting the background field, wherein a difference between the measured one or more optical signals and a signal associated with a sum of the correction optical field and the background optical field is below a selected tolerance level; and extracting one or more characteristics associated with the one or more structures utilizing the correction optical field.

A method for determining one or more optical characteristics of a structure is disclosed. In one aspect, the method may include, but is not limited to, measuring one or more optical signals from one or more structures of a sample; determining a background optical field associated with a reference structure having a selected set of nominal characteristics based on the one or more structures; determining a correction optical field suitable for at least partially correcting the background field, wherein a difference between the measured one or more optical signals and a signal associated with a sum of the correction optical field and the background optical field is below a selected tolerance level; and extracting one or more characteristics associated with the one or more structures utilizing the correction optical field.

In another aspect, a method may include, but is not limited to, determining a background optical field associated with a reference structure having a selected set of nominal characteristics based on the one or more structures; measuring one or more optical signals from one or more structures of a sample; determining a correction optical field suitable for at least partially correcting the background field; determining an expected optical signal utilizing the background optical field and the correction optical field; comparing the expected optical signal to the one or more measured optical signals in order to determine a level of convergence of the expected optical signal with respect to the one or more measured optical signals; and upon detecting a level of convergence below a selected level, extracting one or more characteristics associated with the one or more structures utilizing the correction optical field.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIGS. 4B-4D are schematic views of a small structure disposed on a complex structure, in accordance with various embodiments of the present invention.

FIGS. 5A-5C are schematic views of a previously measured structure having additional material or structures disposed thereon, in accordance with various embodiments of the present invention.

DETAILED DESCRIPTION OF THE INVENTION

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention. Reference will now be made in detail to the subject matter disclosed, which is illustrated in the accompanying drawings.

Referring generally to FIGS. 1A through 12, a system 100 for determining one or more optical signals of a structure 107 is described in accordance with the present invention. In one aspect, the present invention is directed to a system and method for determining optical reflectivity, diffraction, or scattering from a structure 107 of a semiconductor sample 102. In this sense, the system and methods of the present invention determine one or more optical signals (e.g., optical reflectivity, diffraction, or scattering) from a structure of a semiconductor wafer by computing a background optical field for a reference structure and a correction optical field, whereby the correction field is a correction to the background field such that the sum of the background and correction fields are substantially similar to the measured or inspected optical field of the structure.

Figure 1A:
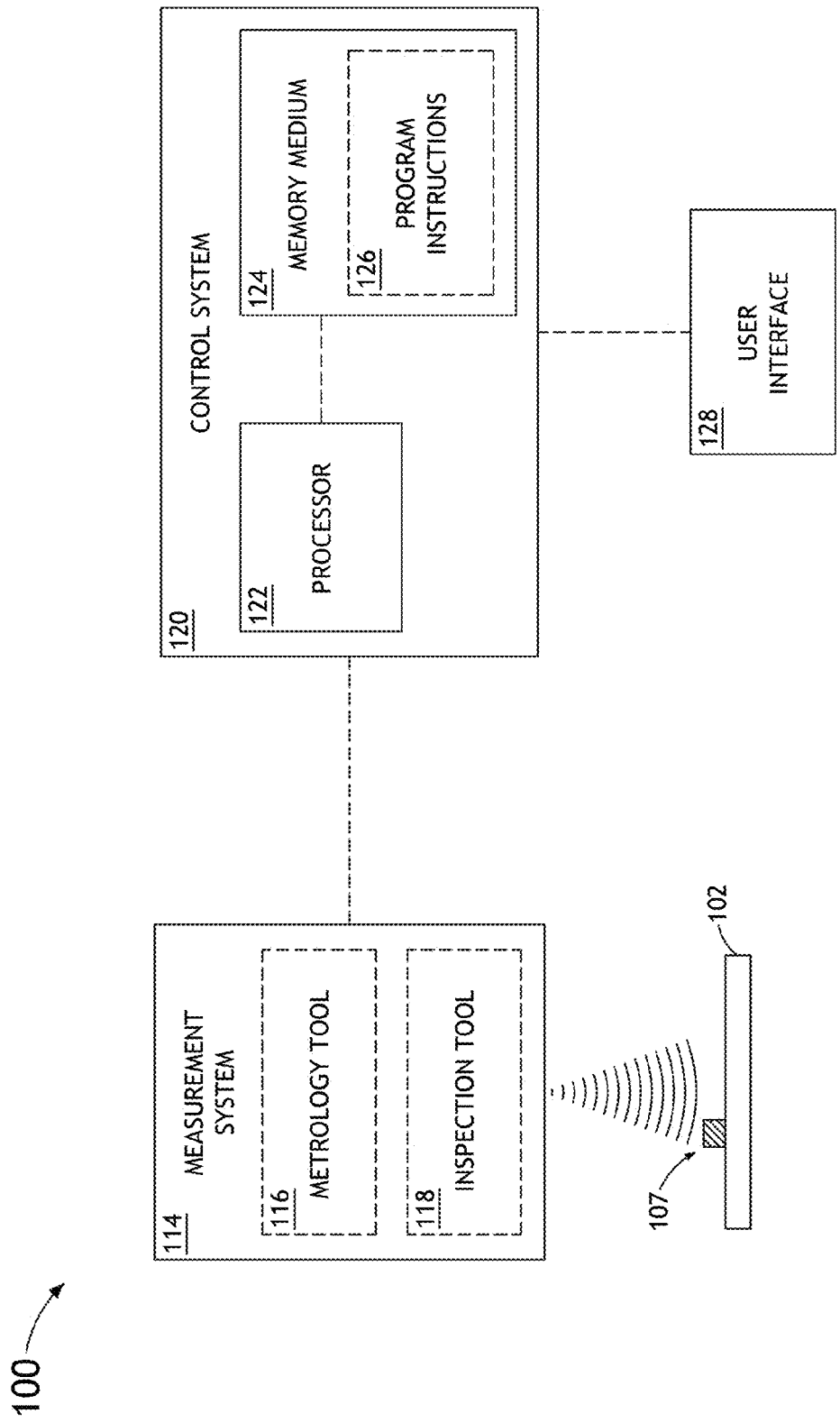
FIG. 1A is a block diagram view of a system for determining one or more optical characteristics of a structure, in accordance with one embodiment of the present invention.

FIG. 1A illustrates a block diagram view of the system 100 for determining one or more optical signals of a structure, in accordance with one embodiment of the present invention. In one embodiment, the system 100 includes a computer control system 120 equipped with one or more processors 122. In another embodiment, the computer control system 120 may further include a non-transitory storage medium 124 (i.e., memory medium) containing program instructions 126 configured to cause the one or more processors 122 to carry out the various steps and embodiments described through the present disclosure. In an additional embodiment, the system 100 includes one or more optical measurement systems 114 (e.g., optical metrology tool 116 or inspection tool 118) configured to measure one or more optical characteristics of one or more structures 107 of a sample 102 (e.g., semiconductor wafer).

In one aspect of the present invention, the one or more processors 122 of the control system 120 are configured to: i) receive one or more measured optical signals of the one or more structures 107 from the optical measurement system 114; ii) determine a background optical field $E_b$ associated with a reference structure, whereby the reference structure may consist of a structure having a selected set of nominal characteristics (e.g., nominal dimensions, nominal shape, and the like) based on the one or more measured structures 107; iii) determine a correction optical field $E_c$ suitable for correcting the background optical field $E_b$ such that the sum of the correction optical field and the background optical field is at least substantially similar (i.e., smaller than a selected tolerance level) to the measured optical field E from the structure 107 of the sample 102; iv) extracting one or more characteristics of the one or more structures 107 utilizing the correction optical field and the background optical field.

For the purposes of the present disclosure, the term "processor" may be broadly defined to encompass any device having one or more processors, which execute instructions from a memory medium. In this sense, the one or more processors 122 may include any microprocessor-type device configured to execute software algorithms and/or instructions. In one embodiment, the one or more processors 122 may consist of a desktop computer or other computer system (e.g., networked computer) configured to execute a set of program instructions 126 configured to operate the system 100, as described throughout the present disclosure. It should be recognized that the steps described throughout the present disclosure may be carried out by a single computer system or, alternatively, multiple computer systems. Moreover, different subsystems of the system 100, such as the measurement system 114 or the user interface device 128, may include a processor or logic elements suitable for carrying out at least a portion of the steps described throughout the present disclosure. Therefore, the above description should not be interpreted as a limitation on the present invention but merely an illustration.

In another aspect, the one or more processors 122 are in communication with the memory medium 124. The memory medium 124 may be configured to store one or more sets of measurement data in a measurement database (not shown). In this regard, the one or more processors 122 of the control system 120 may store all or a portion of the measurement data received by the one or more processors 122 (e.g., received from the measurement device 14, received from an additional system or tool, received from a portable memory medium, such as a solid state memory device, an optical memory device, a magnetic memory device, and the like) in the measurement database maintained in memory 124. In addition, the one or more memory media 124 may store the program instructions suitable for execution by the communicatively coupled one or more processors 122. Program instructions 126 implementing methods such as those described herein may be transmitted over or stored on a carrier medium. The carrier medium may be a transmission medium such as a wire, cable, or wireless transmission link. The carrier medium may also include a memory medium 124 such as a read-only memory, a random access memory, a magnetic or optical disk, or a magnetic tape.

In one aspect of the present invention, the one or more processors 122 of the control system 120 may be configured to divide the problem of solving Maxwell's equations for the optical signal of the structure 107 into two separate problems, allowing for more efficient computation than in the direct computational case. In this sense, the complex amplitude of the propagating polarized wave as a function of location and frequency is represented by the vector E ($\omega$, x, y, z), whereby E represents the spatial distribution of the electric field (i.e., optical field) including the illuminating radiation, the reflected radiation, scattered or diffracted from the structure, and radiation that propagates into the structure. It is noted herein that $\omega$ represents the frequency of the radiation, with (x, y, z) representing the spatial coordinate system (in this example a Cartesian coordinate system). In addition, the time dependence of the electric field is provided by is E ($\omega$, x, y, z)$e^{-i\omega t}$. The electric field (i.e., optical field) associated with the given structure may be written as follows:

$$E = E_B + E_C \quad \text{(Eq. 1)}$$

where E represents the electric field for the structure being measured. In this regard, $E_B$ represents the electric field associated with a reference structure, or related structure, which is similar, but not identical to, the measured structure. Further, $E_C$ represents the electric field of the correction field, which is suitable for correcting the background field $E_B$ such that the sum of $E_B$ and $E_C$ is substantially equal to the measured field E.

It is recognized herein that the measured field E may be a solution to Maxwell's equation. As such, E must satisfy the following relationship:

$$\nabla \times \left( \frac{1}{\mu} \nabla \times \vec{E} \right) - k_0^2 \varepsilon \vec{E} = 0 \quad \text{(Eq. 2)}$$

where $\varepsilon$ and $\mu$ represent the relative permittivity and permeability respectively, c represents the velocity of light in vacuum, and $k_0$ represents the vacuum wave number given by:

$$k_0 = \frac{\omega}{c} \quad \text{(Eq. 3)}$$

It is further noted herein that background optical field $E_B$ must also satisfy Maxwell's equation such that:

$$\nabla \times \left( \frac{1}{\tilde{\mu}} \nabla \times \vec{E}_B \right) - k_0^2 \tilde{\varepsilon} \vec{E}_B = 0 \quad \text{(Eq. 4)}$$

where $\tilde{\varepsilon}$ and $\tilde{\mu}$ represent the relative permittivity and permeability respectively as functions of position for a reference structure. Applicants note that there are many different ways in which the reference structure may differ from the given structure of interest. Examples of how the two structures may differ are described throughout the present disclosure.

It is further noted herein that Eq. 1 may be used to substitute for E in Eq. 2. In turn, utilizing Eq. 4, an expression relating $E_c$ in terms of $E_B$ is given by:

$$\nabla \times \left( \frac{1}{\mu} \nabla \times \vec{E}_C \right) - k_0^2 \varepsilon \vec{E}_C = \nabla \times \left( \left( \frac{1}{\tilde{\mu}} - \frac{1}{\mu} \right) \nabla \times \vec{E}_B \right) - k_0^2 (\tilde{\varepsilon} - \varepsilon) \vec{E}_B \quad \text{(Eq. 5)}$$

In one embodiment, Eq. 5 may be solved by the one or more processors 122 of the control system 120 using finite element analysis. In settings where the structural characteristics of the structure are such that $\tilde{\varepsilon}$ is at least approximately equivalent to $\varepsilon$ and $\tilde{\mu}$ is at least approximately equal to $\mu$, the right-hand side of Eq. 5 tends toward zero. As such, the mesh of points used for finite element analysis may be relatively sparse (i.e., typically a spacing of mesh between approximately an eighth and a quarter of the wavelength in the given region is appropriate for most regions where the right-hand side is zero or approximately zero). It is further noted that near the boundary between the region where the right-hand side of Eq. 5 is substantially zero and the region where it is substantially non-zero, a denser mesh may be preferred. In cases where the boundary represents a small fraction of the total volume, the extra computation for this may be relatively small, while the accuracy of the calculation may be significantly improved compared with a sparse mesh in the boundary region.

In contrast, in regions where the right-hand side of Eq. 5 is substantially non-zero, the finite element analysis carried out by the one or more processors 122 may require a denser mesh. In another embodiment, in settings where $\tilde{\varepsilon}$ and $\tilde{\mu}$ represent a structure for which the solution $E_B$ is known or for which the solution for $E_B$ may be straightforwardly computed, the computation of $E_C$ by the one or more processors 122 may be efficient if the region(s) over which either or both $\tilde{\varepsilon}$ and $\tilde{\mu}$ differ significantly from $\varepsilon$ and $\mu$ are small compared to the size of the entire structure 107.

In another embodiment, the algorithm and/or boundary conditions used by the one or more processors 122 to solve Eq. 5 may differ from those used to compute the background field $E_B$. It is further noted that the correction field $E_C$ may only need be computed over substantially the region for which it is non-negligible compared with $E_B$ (where a negligible difference is a difference smaller than the noise level of system 100).

Applicants note that most, but not all, materials commonly used in the semiconductor industry are non-magnetic (i.e. $\mu=1$ everywhere). In settings where only non-magnetic materials are implemented, Eq. 5 may be simplified to give:

$$\nabla \times \nabla \times \vec{E}_C - k_0^2 n^2 \vec{E}_C = k_0^2 (\tilde{n}^2 - n^2) \vec{E}_B \quad \text{Eq. 6}$$

where $E_B$ represents the electric field for a reference non-magnetic structure with $\tilde{\mu}=1$ everywhere, n is the complex refractive index (equal to $\sqrt{\varepsilon}$), and $\tilde{n}$ is the complex refractive index (equal to $\sqrt{\tilde{\varepsilon}}$) for the reference non-magnetic structure.

In this regard, the control system 120 may be configured to receive an instruction signal from the user interface device 128 indicative of the type of material being analyzed by system 100. In settings where the structure 107 is magnetic, the one or more processors may be configured to apply Eq. 5 (or some variation thereof), while in settings where the structure 107 is substantially non-magnetic, the one or more processors may be configured to apply Eq. 6 (or some variation thereof). The remainder of this disclosure will discuss various implementations of the present invention.

In one embodiment, the measurement system 114 of system 100 may include, but is not limited to, any optical metrology tool 116 known in the art. For example, the measurement system 114 may include, but is not limited to, a reflectometer (e.g., beam profile reflectometer) suitable for measuring one or more optical metrology parameters. By way of another example, the measurement system 114 may include, but is not limited to, an ellipsometer (e.g., beam profile ellipsometer) suitable for measuring one or more optical metrology parameters. The one or more optical metrology parameters may include, but are not limited to, critical dimension (CD), shape, size and the like of one or more structures 107 of a semiconductor wafer 102. A combined ellipsometer/reflectometer system suitable for implementation in the measurement system 114 is described by Piwonka-Corle et al. in U.S. Pat. No. 5,608,526, issued on Mar. 4, 1997, which is incorporated herein in the entirety. A beam profile reflectometer and beam profile ellipsometer suitable for implementation in the measurement system 114 are described by Gold et al. in U.S. Pat. No. 4,999,014, issued on Mar. 12, 1991; Fanton et al. in U.S. Pat. No. 5,181,080, issued on Jan. 19, 1993; Opsal et al. in U.S. Pat. No. 6,429,943, issued on Aug. 6, 2002; and Opsal in U.S.

Pat. No. 6,678,046, issued on Jan. 13, 2004, which are each incorporated herein by reference in their entirety.

In another embodiment, the measurement system 114 of system 100 may include, but is not limited to, any optical inspection tool 118 known in the art. For example, the measurement system 114 may include, but is not limited to, a dark-field inspection system. By way of another example, the measurement system 114 may include, but is not limited to, a dark-field inspection system or a bright-field inspection system. Optical inspection tools suitable for implementation in the measurement system 114 are described by Jann et al. in U.S. Pat. No. 5,189,481, issued on Feb. 23, 1993; Vaez-Iravani et al. in U.S. Pat. No. 6,201,601, issued on Mar. 13, 2001; Marx et al. in U.S. Pat. No. 6,271,916, issued on Aug. 7, 2001; Leong et al. in U.S. Pat. No. 7,525,649, issued on Apr. 28, 2009; Kvamme et al. in U.S. Pat. No. 7,352,457, issued on Apr. 1, 2008; and Chuang et al. in U.S. Publication No. 2007/0002465, published on Jan. 4, 2007, which are each incorporated herein by reference in their entirety.

In an additional embodiment, the system 100 may include a user interface device 128 communicatively coupled to the computer control system 120. The user interface device 128 may include, but is not limited to, a display device and a user input device communicatively coupled to the one or more processors 122 of the control system 120. The display device may include any display device known in the art. In one embodiment, the display device may include, but is not limited to, a liquid crystal display (LCD). In another embodiment, the display device may include, but is not limited to, an organic light-emitting diode (OLED) based display. In another embodiment, the display device may include, but is not limited to a CRT display. Those skilled in the art should recognize that a variety of display devices may be suitable for implementation in the present invention and the particular choice of display device may depend on a variety of factors, including, but not limited to, form factor, cost, and the like. In a general sense, any display device capable of integration with a user interface device (e.g., touchscreen, bezel mounted interface, keyboard, mouse, trackpad, and the like) is suitable for implementation in the present invention.

The user input device may include any user input device known in the art. For example, the user interface may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. In the case of a touchscreen interface device, those skilled in the art should recognize that a large number of touchscreen interface devices may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of the display device is suitable for implementation in the present invention. In another embodiment, the user interface may include, but is not limited to, a bezel mounted interface. In the case of a bezel input device, the display device may include a bezel equipped with one or more bezel mounted interface devices. For instance, the bezel mounted interface may include, but is not limited to, a hard key (or hard "button") disposed on the bezel of the display device. In a general sense, any bezel mounted interface capable of integration with the display device is suitable for implementation in the present invention.

Figure 1B:
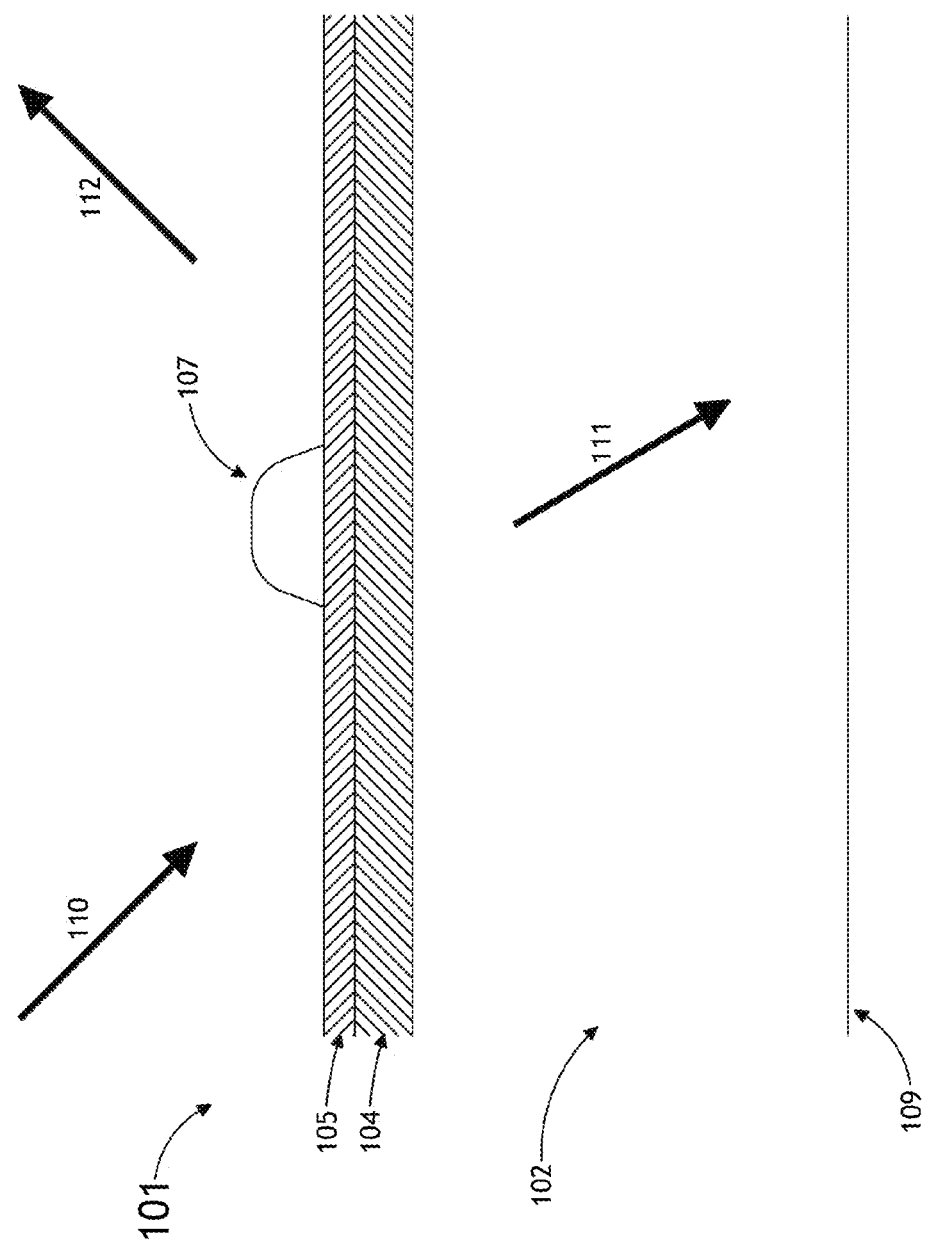
FIG. 1B is a cross-sectional view of a structure disposed on a semiconductor wafer, in accordance with one embodiment of the present invention.

FIG. 1B illustrates a high level cross-sectional view 101 of a semiconductor wafer 102 having a first layer 104, a second layer 105, and a structure 107 disposed thereon, in accordance with one embodiment of the present invention. Applicants note that the depiction of a first layer 104 and a second layer 105 disposed on the surface of the wafer 102 should not be interpreted as a limitation and is provided merely for illustrative purposes. It is recognized herein that the present invention is applicable to samples, such as semiconductor wafers, having 0, 1, 2, and up to and including N layers formed thereon.

In one embodiment, the structure 107 may include, but is not limited to, a particle disposed on the surface of the wafer 102 or the surface of one or more layers 104, 105. For example, the structure 107 may include, but is not limited to, a contaminant particle disposed on the surface of the wafer 102 or the surface of one or more layers 104, 105.

In another embodiment, the structure 107 may include, but is not limited to, a structure fabricated on the surface of the wafer 102 or the surface of one or more layers 104, 105. In a further embodiment, the structure 107 may include, but is not limited to, a regular geometric pattern of a structure fabricated on the surface of the wafer 102 or the surface of one or more layers 104, 105. For example, the regular geometric pattern structure may include, but is not limited to, a test structure or metrology structure (e.g., CD metrology structure, overlay metrology structure, and the like). By way of another example, the regular geometric pattern structure may include, but is not limited to, a circuit or circuit structure.

In another aspect, incident radiation 110 emanates from a light source (not shown in FIG. 1B) and illuminates a region of the surface of the sample 102 including structure 107. It is noted herein that, while FIG. 1B depicts the radiation 110 as being transmitted along one direction, the radiation 110 incident on the sample 102 may consist of illumination from incident on the sample from many directions, such as, but not limited to, illumination from high numerical aperture (NA) optics.

In some embodiments, the radiation 110 emanating from a light source may include, but is not limited to, single wavelength light, multiple wavelength light or continuous wavelength light. In additional embodiments, the radiation 110 emanating from the light source may include, but is not limited to, vacuum UV light, deep UV light, near UV light, visible light or infrared light.

In another aspect, the radiation emanating from the light source may be transmitted by the sample 102 and/or reflected, scattered, and/or diffracted by the wafer 102. As shown in FIG. 1B, radiation 111 is transmitted into the sample 102 (e.g., semiconductor wafer). It is recognized herein that for most wavelengths of interest the radiation is absorbed by the wafer 102. In contrast, for some wavelengths, such as infrared radiation, the radiation 111 transmitted into the sample 102 may reach the lower surface 109 of the sample 102 and may reflect off of the lower surface 109. As shown in FIG. 1B, the radiation 112 is reflected, scattered and/or diffracted from the wafer 102 along one or more directions, allowing for detection using a detector (not shown). It is noted herein that, while FIG. 1B depicts the reflected, scattered, or diffracted radiation 112 as being directed along one direction, the radiation may be directed in one or multiple directions. In a further embodiment, the radiation 112 may be diffracted along multiple discrete directions corresponding to the diffraction orders associated with the structure 107. In a general sense, the radiation fields 110, 111, and 112 and the electric fields inside the structure 107 and/or the film layers 104, 105 and/or the sample 102 may be written symbolically as E(ω, x, y, z).

In one embodiment of the present invention, the one or more processors 122 of the control system 120 may calculate the background field $E_B$ for a sample such as that depicted in FIG. 1B. In this regard, one or more processors 122 may calculate the background field $E_B$ for a planar structure that consists of only the wafer 102 and the film layers 104, 105 (if film layers are present). In a further embodiment, the one or more processors 122 may calculate the Fresnel reflectivity and, thus, determine the background field $E_B$. It is noted herein that a variety of computation methods known in the art may be utilized to calculate the background field $E_B$ based on a simplified wafer/film layer structure. In one embodiment, upon determining $E_B$, the correction field $E_C$ may be calculated using a finite element method by solving Eq. 6 described previously herein, whereby the right-hand side of Eq. 6 is non-zero only for the volume occupied by structure 107. In another embodiment, in settings where structure 107 includes one or more magnetic materials, the correction field $E_C$ may be calculated using a finite element method by solving Eq. 5 described previously herein, whereby the right-hand side of Eq. 5 is non-zero only for the volume occupied by structure 107.

FIGS. 2A-2D illustrate cross-sectional views of various sample configurations to which the present invention is applicable, in accordance with embodiments of the present invention. While FIG. 1B depicts a setting wherein the structure 107 is disposed entirely on the sample 102 surface, FIGS. 2A-2D depict settings where the structure 107 is partially or completely embedded in the surface of the sample or completely below the surface of the sample 102. It is noted herein that the structure 107 may consist of a different material within the sample/layer volume, excess material within the sample/layer volume, or missing material within the sample/layer volume.

Figure 2A:
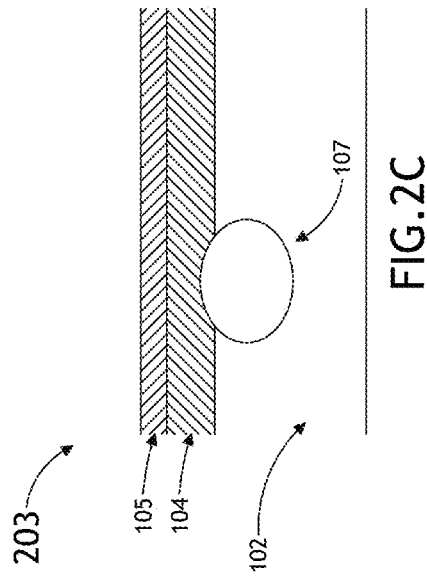
FIG. 2A is a cross-sectional view of a partially embedded and protruding structure of a semiconductor wafer, in accordance with one embodiment of the present invention.

In one embodiment, as shown in FIG. 2A, the cross-sectional view 201 depicts a sample/structure arrangement wherein the structure (e.g., fabricated structure, particle, or void) is partially embedded and partially protruding from the one or more surface layers (e.g., layers 104, 105) of the sample.

Figure 2C:
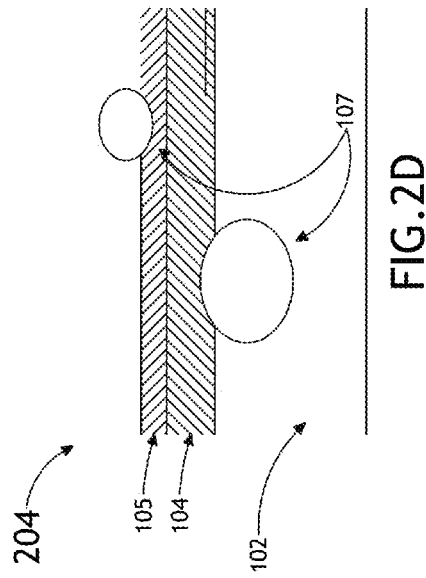
FIG. 2C is a cross-sectional view of a structure of a semiconductor wafer disposed below one or more surface layers, in accordance with one embodiment of the present invention.
Figure 2B:
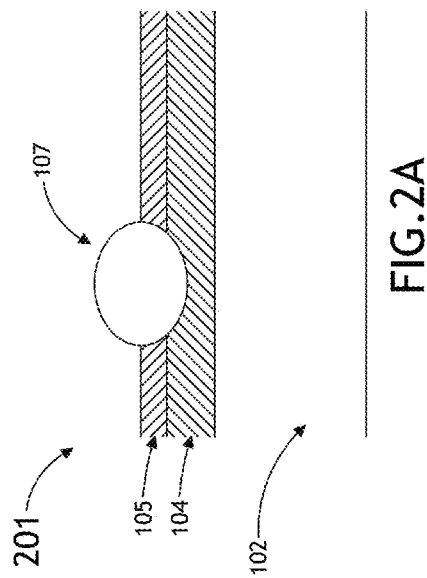
FIG. 2B is a cross-sectional view of a structure of a semiconductor wafer consisting of a void of material, in accordance with one embodiment of the present invention.

In another embodiment, as shown in FIG. 2B, the cross-sectional view 202 depicts a sample/structure arrangement wherein the structure 107 consists of a void of material from one or more surface layers (e.g., layers 104, 105) of the sample.

In another embodiment, as shown in FIG. 2C, the cross-sectional view 203 depicts a sample/structure arrangement wherein the structure 107 (e.g., fabricated structure, particle, or void) is disposed below the one or more surface layers (e.g., layers 104, 105) of the sample.

Figure 2D:
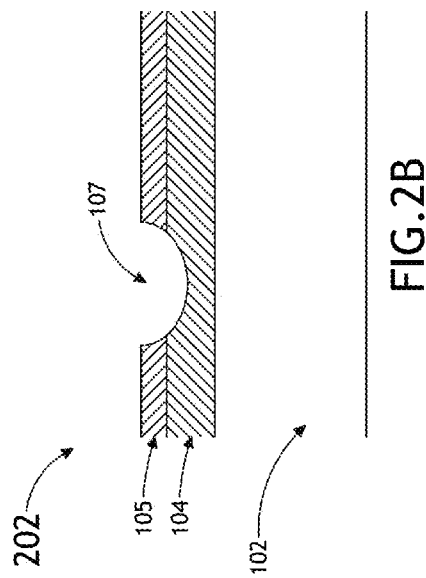
FIG. 2D is a cross-sectional view of a structure of a semiconductor wafer formed of structure material located in two or more distinct regions, in accordance with one embodiment of the present invention.

In another embodiment, as shown in FIG. 2D, the cross-sectional view 204 depicts a sample/structure arrangement wherein the structure 107 material (e.g., fabricated structure, particle, or void) is located in two or more distinct regions of the sample. For example, a first portion of the structure 107 may be disposed within the wafer 102 and layer 104, while a second portion of the structure 107 may be partially embedded in surface layer 105, as shown in FIG. 2D.

It is noted herein that for the configurations depicted in FIG. 1B and FIGS. 2A-2D the background electric field $E_B$ may be computed by the one or more processors 122 by calculating the planar structure assuming the structure contains no additional material or voids, as described previously herein.

Figure 3:
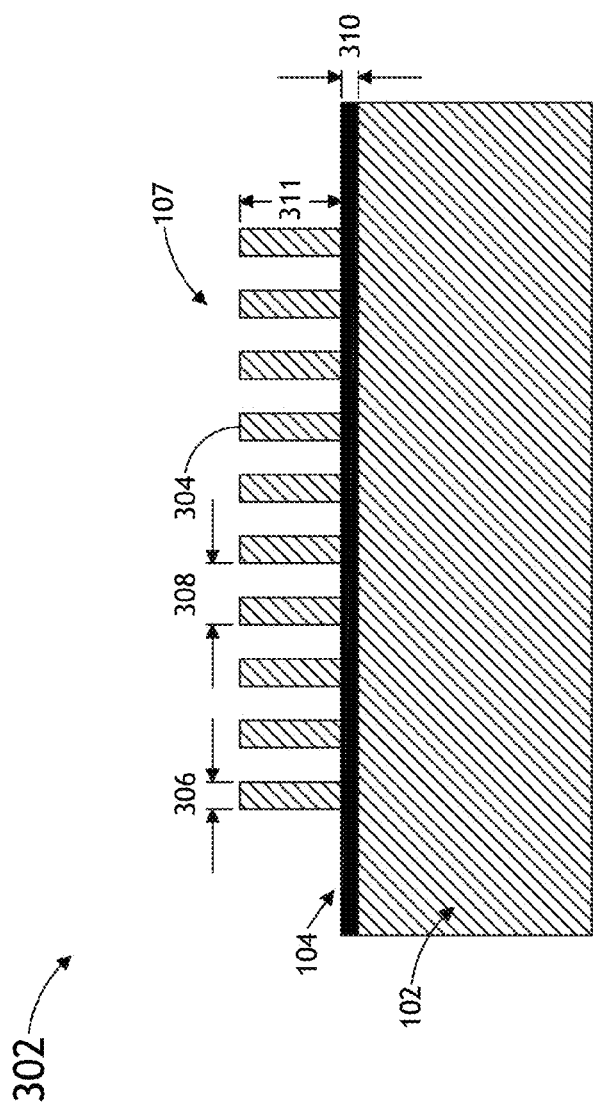
FIG. 3 is a cross-sectional view of a structure having small and periodic features disposed on a semiconductor wafer, in accordance with one embodiment of the present invention.

FIG. 3 illustrates a cross-sectional view 302 of a "small" periodic structure 107 disposed on the surface of the wafer 102 or the film layer(s) 104 or 105. In one embodiment, the "small" periodic structure 107 may include a series of simple structures 304 aligned periodically with respect to one another. For example, the periodic structure 107 of FIG. 3 may include a series of rectangular elements 304 disposed on one or more layers 104, 105 having a thickness 310 and aligned along the horizontal direction, with each element having a selected thickness 306 and height 311, whereby the elements are spaced apart by a selected spacing 308. For example, the small periodic structure 107 of FIG. 3 may consist of ten rectangular elements 304 aligned horizontally with a spacing of 40 nm, whereby each element 304 is at least approximately 80 nm tall and 20 nm wide and disposed on a film layer having a 2 nm thickness.

In another embodiment, the structure 107/film 104/wafer 102 assembly may be formed from two materials. For example, the periodic structure 107 of FIG. 3 may be formed from Si, while the one or more film layers may consist of a $SiO_2$ layer grown on a Si wafer 102. Applicants note that the present invention is not limited to a particular type of material and the above materials are listed merely for illustrative purposes.

It is recognized herein that embodiments of the present invention, such as those depicted in FIG. 3, may be used to compute the reflectivity and scattering from the structure 107 regardless of the complexity of the implemented structure (e.g., complexity of shapes or number of different materials used in the structure). For example, in the case of a binary material system, $E_B$ may be computed from the Fresnel reflection and transmission coefficients for the first material (e.g., silicon dioxide) disposed on the second material (e.g., silicon) structure. Applicants further note that an algorithm, such as RCWA, that computes reflectivity of a periodic structure cannot generally be used for a structure such as that shown in FIG. 3 due to the small spatial extent of the structure. This is a result of the width of the structure (e.g., approximately 380 nm for the example described above) being smaller than the illuminated area (e.g., illumination area of 1 μm or larger). As such, the electromagnetic problem to be solved is not periodic. Applicants note, however, that RCWA may be used to approximately compute the reflectivity by assuming that the elements 304 of the periodic structure 107 are repeated on a pitch larger than the given illumination spot. It is further recognized herein that such a computation would be relatively slow because of the large assumed pitch (on the order of microns). Moreover, because a high truncation order would be required to accurately represent features on the order of 20 nm in width such a calculation may be too slow for practical use. Alternatively, a lower truncation order could be used to speed computation, but the result may lack sufficient accuracy.

Figure 4A:
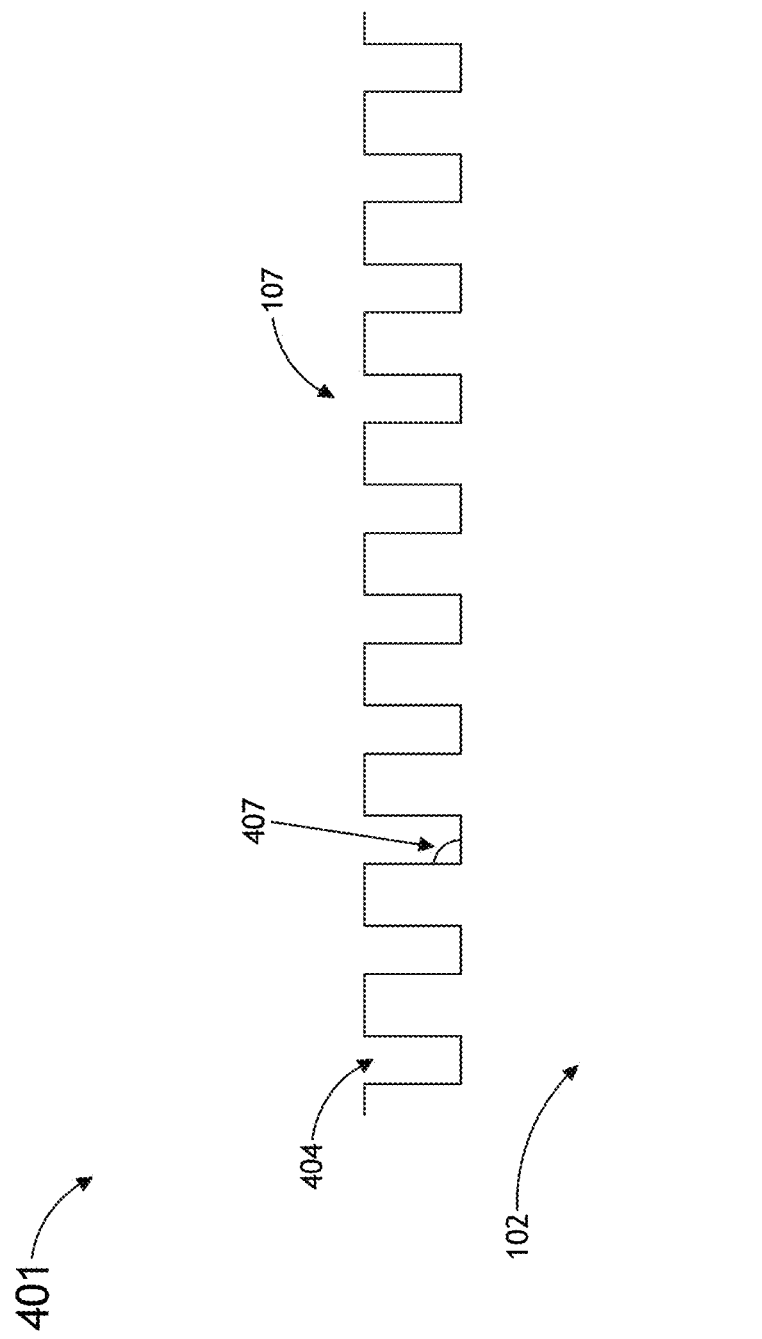
FIG. 4A is a cross-sectional view of a structure consisting of periodic trenches in a semiconductor wafer, in accordance with one embodiment of the present invention.

FIG. 4A illustrates a cross-sectional view 401 of a periodic structure 107 formed from a series of periodic trenches 404 etched into the surface of a semiconductor wafer 102. In one embodiment, a volume of material 407 may be present in one or more of the trenches 404. In a further embodiment, the extra material may include, but is not limited to, a particle, residue from an etching process or material left over from an incomplete etching process. In accordance with the various embodiments of the present invention, the reflectivity, diffraction and/or scattering of the structure 107 may be calculated by first calculating a background field $E_B$ for the regular series of trenches 404 without the extra material 407. Then, the correction field $E_C$ may be calculated to account for the extra material 407, in accordance with Eq. 6 (or Eq.

5 in the case of magnetic materials) described previously. Applicants further note that this procedure may also be applied when there is missing material (not shown in FIG. 4A) in one or more of the trenches 404. In a further embodiment, the extra or missing material 407 may be positioned at the bottom of a trench 404, partially up a wall of the trench 404, at (or near) the top of the trench 404, or embedded in the structure below the trenches 404.

Figure 4B:
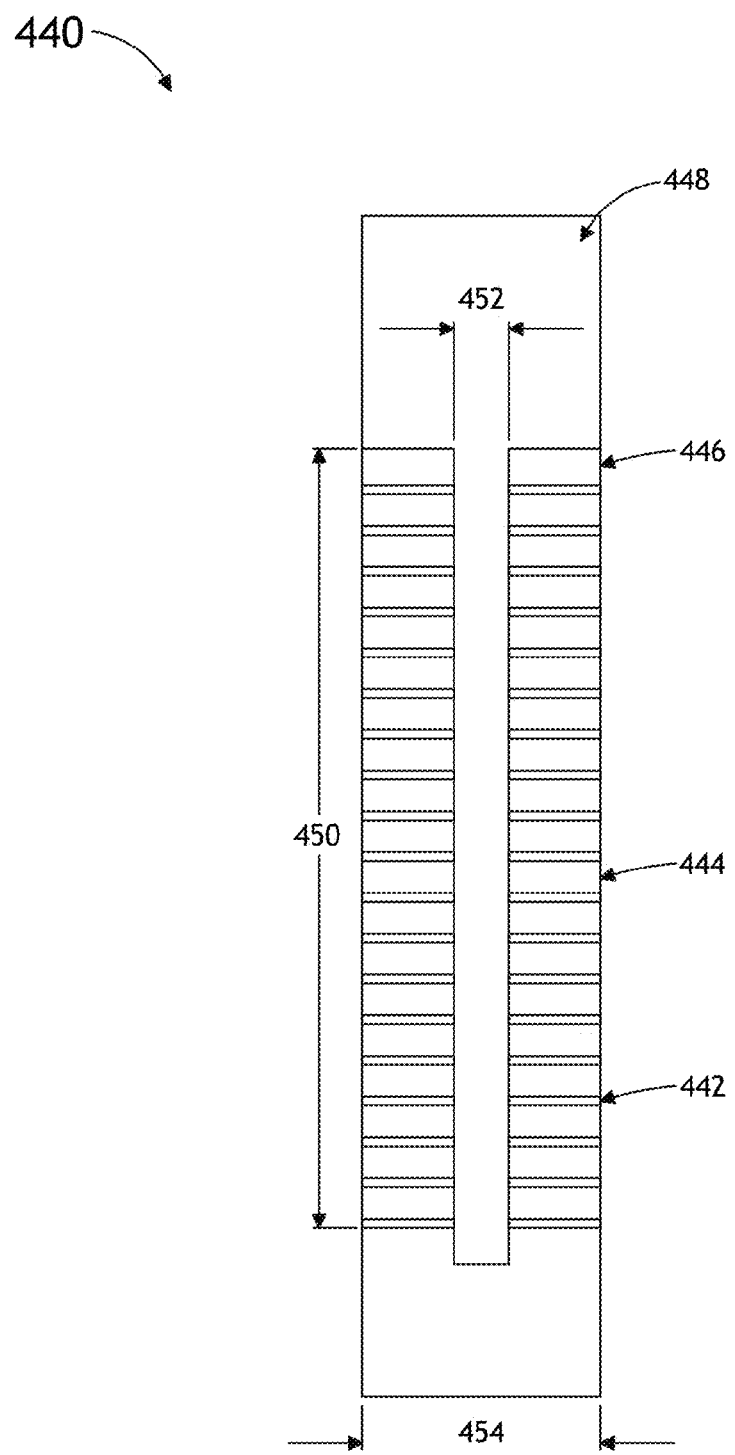
Figure 4D:
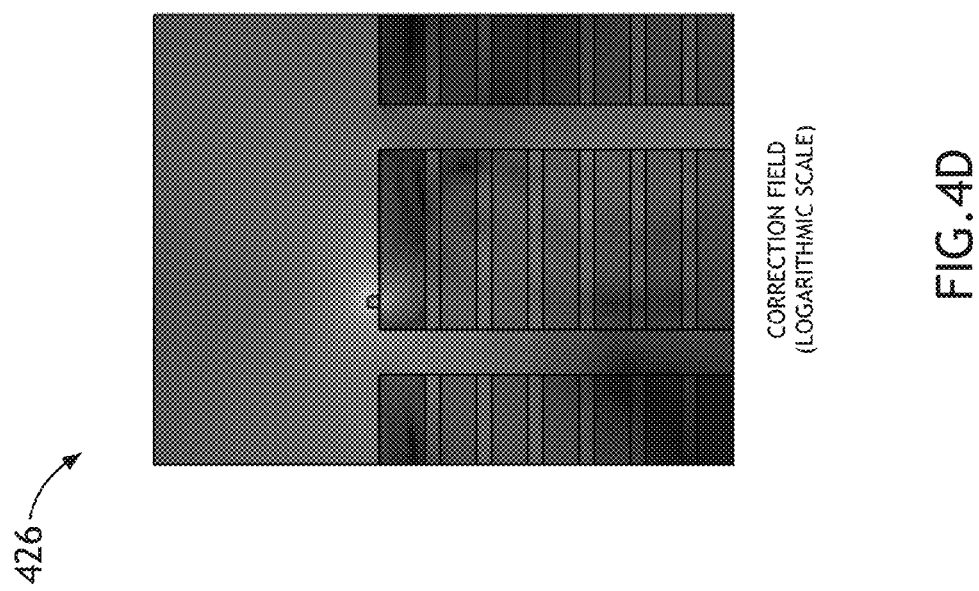

FIGS. 4B-4D illustrate a "small" feature disposed on top of a complex structure, in accordance with one embodiment of the present invention. In one aspect, FIG. 4B depicts a cross-sectional conceptual view of a unit cell 440 of a structure similar to a portion of a three-dimensional FLASH memory structure. FLASH memory structures are described generally by Katsumata el al. "Pipe-shaped BiCS Flash Memory with 16 Stacked Layers and Multi-Level-Cell Operation for Ultra High Density Storage," 2009 Symposium on VLSI Technology Digest of Technical Papers, 136-137, which is incorporated herein by reference in the entirety.

As shown in FIG. 4B, the pattern is periodic along one direction, while having a constant cross-section in the perpendicular direction. In one embodiment, the structure may include multiple layers of material, as shown in FIG. 4B. In a further aspect, the periodic structure 440 may include a pitch 454 (e.g., 500 nm), a trench width 452 (e.g., 100 nm), a trench depth (e.g., 2.25 µm). In an additional embodiment, the periodic structure 440 may include a selected number of layers 442 of a first material along the trench direction (vertical in FIG. 4B), with a selected number of layers 444 of a second material interposed between the first material layers 442. For example, the structure 440 may include 19 layers 442 of silicon dioxide, which alternate with 18 layers of silicon nitride 444. It is further noted that additional materials suitable for implementation in the structure 440 may include, but are not limited to, amorphous or polycrystalline silicon.

In another embodiment, the structure 440 may include a hard-mask material 446 disposed on top of the alternating layers 442, 444. In one embodiment, the hard-mask material 446 may include, but is not limited to, silicon-rich silicon nitride, titanium nitride or amorphous silicon. Applicants further note that an ambient medium 448 (e.g., air) may be located above the hard-mask material 446.

FIG. 4C illustrates a series of images depicting the background, correction, and total fields, in accordance with one embodiment of the present invention. Image 420 in FIG. 4C depicts the field amplitude for the background field $E_B$ computed for the repeating structure superimposed on top of an image of a portion of two unit cells of the structure 440. In this illustration, the lightest regions of the image 420 represent a field amplitude of 2 and the darkest regions of the image 420 represent a field amplitude of 0, with the incident light having an amplitude of 1. It is noted herein that the field amplitude of 2 occurs in regions of constructive interference.

Image 422 in FIG. 4C depicts conceptually the field amplitude for the correction field $E_c$ for a rod (e.g., 25 nm by 25 nm rod) of silicon disposed on top of the structure 440 superimposed on an image of the structure 440. Applicant notes that the structure 440 is difficult to view because the field is mostly black (i.e., near 0 amplitude). It is further noted herein that the correction field $E_c$ is weak compared with the background field $E_B$. Therefore, when plotted with the same scale as the background field, the only visible field is in and immediately adjacent to the silicon rod, which appears as a light hazy region in image 422. For further illustration, FIG. 4D depicts the correction field plotted on a logarithmic scale so as to show more clearly the weaker features and their relationship with the underlying structure 440. This figure illustrates that small changes to the background field can be calculated utilizing the procedure of the present invention. It is further noted herein that directly calculating the field for the entire problem to this level of accuracy would require a much finer and larger mesh as well as a correspondingly long computation time when compared to separating the problem into two separate calculations, as done in the present invention.

Image 424 in FIG. 4C depicts conceptually the field amplitude for the total field $E_T$ superimposed on an image of the structure 440, whereby the total field consists of a sum of the background field $E_B$ and correction field $E_C$, as governed by Eq. 1. Applicant notes that the structure 440 is difficult to view because the field is mostly black (i.e., near 0 amplitude).

It is noted herein that the principles illustrated by the example depicted in FIGS. 4B-4D may be extended to patterns that are periodic in two dimensions. Additionally, the principles illustrated by the example depicted in FIGS. 4B-4D may be extended to the narrow rod where a small particle or defect is localized on all three dimensions.

FIGS. 5A-5C illustrate a series of embodiments wherein additional material and/or structures are added to a previously measured or calculated structure. FIG. 5A depicts a cross-sectional view of a structure 501 consisting of a single unit cell of a repeating structure etched into a surface 502, in accordance with one embodiment of the present invention. It is noted herein that, although the structure 501 in FIG. 5A is depicted as if the cross-section is constant in one direction (i.e. the unit cell is two-dimensional, repeating in only one direction), the unit cell may also be three-dimensional (i.e., repeating in two different directions), with the same or different pitches in those two directions. In another aspect, the fields discussed previously herein may be calculated for this structure using any known algorithm including, but not limited to, RCWA, Green's functions, FDTD or finite element methods. In a further aspect, the field calculation may be performed as part of the measurement or inspection process of the structure.

FIG. 5B depicts a cross-sectional view of a composite structure 510 consisting of additional material or materials 512 deposited or grown on the surface of the repeating structure 501 formed in the surface 502 (shown in FIG. 5A, in accordance with one embodiment of the present invention. In one embodiment, the additional material(s) 512 may be grown on the surface 502 subsequent to at least one of a deposition, polishing, or etching process. In one embodiment, in order to calculate the electric field amplitudes for the new structure 510, the background field $E_B$ may be assumed to be equivalent to the field previously calculated for structure 501. In turn, the extra material(s) 512 may be used to calculate the correction field $E_C$. In a further aspect, in settings where the pitch(es) of the new structure are the same as the previous structure (501), the same periodic boundary conditions may be used in solving the equation for $E_C$ as previously used for calculating $E_B$. It is further noted herein that, since the surface 502 may have been cleaned after the measurement or inspection of structure 501 and/or the deposition of the material 512, the original surface profile 502 may have experienced some modifications via the removal of a small amount of material (e.g., perhaps only equivalent to 1-2 monolayers of atoms). Moreover, the correction field calculation may also include non-zero terms on the right hand side of Eq. 6 (or Eq. 5 in the case of magnetic materials), accounting for a possible change in shape and/or position of the surface 502 occurring prior to the deposition of the material 512.

FIG. 5C depicts a cross-sectional view of an additional composite structure 520 resulting from the formation of an additional structure 522 formed on the structure 510 during one or more additional processing steps (e.g., deposition or etching), in accordance with one embodiment of the present invention. In one embodiment, the additional structure 522 may be fabricated on the top surface of the additional material 512 of structure 510. In another embodiment, the additional structure 522 may include one or more materials. In another embodiment, the additional structure 522 may have the same pitch as structure 510. In another embodiment, the additional structure may have a pitch that is in a simple integer ratio (e.g., 1/3, 1/2, 2, 3, and the like) with the pitch of structure 510. In another embodiment, the number of repeats of structure 522 may be few enough such that the overall structure may be treated as non-repeating.

In one embodiment, the electric field amplitude calculated for the structure 510 may be used for the background field $E_B$ in the calculation of the correction field $E_C$ for structure 520. In the case where structure 520 has the same pitch(es) as the underlying structure 510, or an integer sub-multiple (e.g., pitch 1/2 of the underlying structure), then the pitch of the underlying structure may be used for the periodic boundary conditions for the calculation of $E_C$. In the case where the pitch of the structure 520 is an integer multiple of the pitch of the underlying structure 510, then the pitch of the structure 520 should be used for the periodic boundary conditions in the calculation of $E_C$. In the case where structure 520 is not periodic, then the boundary used for the calculation of $E_C$ will be non-periodic and should be chosen to be large enough such that the magnitude of $E_C$ at the boundary is small relative to $E_B$.

Applicants note that FIGS. 5A-5C are illustrations of settings wherein the present invention may be implemented to determine the fields and optical signals from inspection and/or metrology measurements in a pattern fabrication process involving multiple steps, with inspection and/or metrology measurements performed at multiple points throughout the fabrication process. Applicants further note that instead of computing the optical signals at each step independently from a given inspection or metrology measurement, the calculation at a subsequent step may be based on the results of a calculation carried out at an earlier step. Applicants further note that even if subsequent steps modify the shape, dimensions or optical properties of a prior step, this situation may be accounted for by the $(n^2-\tilde{n}^2)$ term on the right-hand side of Eq. 6 (or the equivalent terms in $\mu$, $\tilde{\mu}$, $\in$ and $\tilde{\in}$ in Eq. 5 in the case of magnetic materials).

Figure 6A:
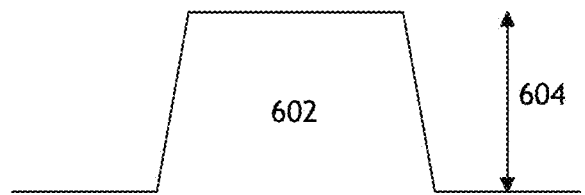
FIG. 6A is a schematic view of a unit cell of a repeating structure on a surface of a sample, in accordance with one embodiment of the present invention.
Figure 6B:
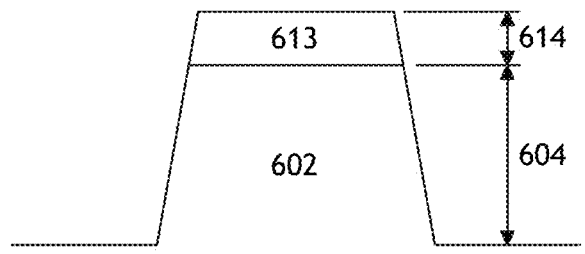
FIG. 6B is a schematic view of a unit cell of a repeating structure having additional material disposed thereon, in accordance with one embodiment of the present invention.

FIGS. 6A and 6B illustrate an additional implementation of the present invention particularly useful in a metrology setting, in accordance with one embodiment of the present invention. FIG. 6A illustrates a cross-sectional view of a structure 601 having a unit cell of a repeating structure on a surface 602.

Applicants again note that, while structure 601 is depicted as two-dimensional with a cross-section that is constant in one direction, the unit cell may be three-dimensional (repeating in two different directions with the same or different pitches in those two directions). In a further aspect, the structure 601 has shape and size features that may be characterized by multiple dimensions. For example, as shown in FIG. 6A, one dimension may include, but is not limited to, the height 604 of the individual structures formed in the surface 602.

Applicants note that even for a simple structure, such as that that depicted in FIG. 6A, requires multiple dimensions to characterize it. However, for the purposes of clarity, the Applicants focus on one of those dimensions. In one embodiment, the shape and the values of all the dimensions of structure 601 may be obtained from a measurement of one or more examples of that structure. In another embodiment, the shape and values of all dimensions for structure 601 may be established via a nominal design. Based on the shape and dimension information, the electric fields may be calculated utilizing any algorithm known in the art including, but not limited to, RCWA, Green's functions, FDTD or finite element methods.

It is noted herein that in order to measure a new article of the same structure, it is necessary to know how the electric fields change with respect to changes in shape and dimension, since each fabricated structure will have slightly different dimensions and/or shape. Traditionally, it is generally necessary to redo the entire electromagnetic calculation in situations where a dimension of the given structure changes. In some cases, analytical derivatives of the electromagnetic signal with respect to dimension changes may be calculated and used to calculate the change in electromagnetic signal for small changes in certain dimensions. Such calculations, however, are only valid for small changes in dimensions and analytical derivatives cannot be calculated for some shape changes. In addition, such calculations may be too complicated to implement for other structural changes.

Applicants further note that the various embodiments of the present invention may be used to recalculate fields for any shape change (small or large) by utilizing the previously calculated field for $E_B$ and then using Eq. 6 (or Eq. 5 if appropriate) to calculate $E_C$ for the changes in the field due to changes in shape or dimensions.

FIG. 6B illustrates a cross-sectional view of structure 611 consisting of additional material 613 formed on the structure 601, in accordance with one embodiment of the present invention. It is noted herein that the structure 611 is similar to the structure 601, but with a taller height equal to h+Δh, whereby h is the height 604 of the structural feature of 601 and the change in height 614 is equal to the height of the additional material 613. In one aspect, in order to calculate the fields for the structure 611, the region wherein the term $(n^2-\tilde{n}^2)$ on the right-hand side of Eq. 6 (or the equivalent terms in Eq. 5) is non-zero corresponds to the extra material 613. In an alternative embodiment, in settings where the height of the structure 611 is lower than the height of structure 601 (i.e. Δh has negative value), then the region where $(n^2-\tilde{n}^2)$ is non-zero corresponds to missing material. It is noted herein that the approach described above may be used for a change in a single dimension (e.g., height or width) or may be extended to more complex shape changes.

It is further noted herein that the calculation of the change in field due to the change in shape of a given structure may be used to predict measurement sensitivity in order to determine the best measurement mode, including the selection of measurement conditions, such as, but not limited to, wavelengths, angles of incidence, azimuth angles and polarization states. The impact of calculations of electromagnetic fields and changes in electromagnetic fields on the development of optical CD metrology recipes is generally described in co-pending U.S. patent application Ser. No. 13/164,398, filed Jun. 20, 2011, which is incorporated herein by reference in the entirety.

It is further recognized that various embodiments of the present invention may be used to carry out real-time regression. Real-time regression for optical CD metrology is described generally in U.S. Pat. No. 7,031,848 to Opsal et al., filed Jul. 8, 2005, which is incorporated herein by reference in the entirety.

Figure 7:
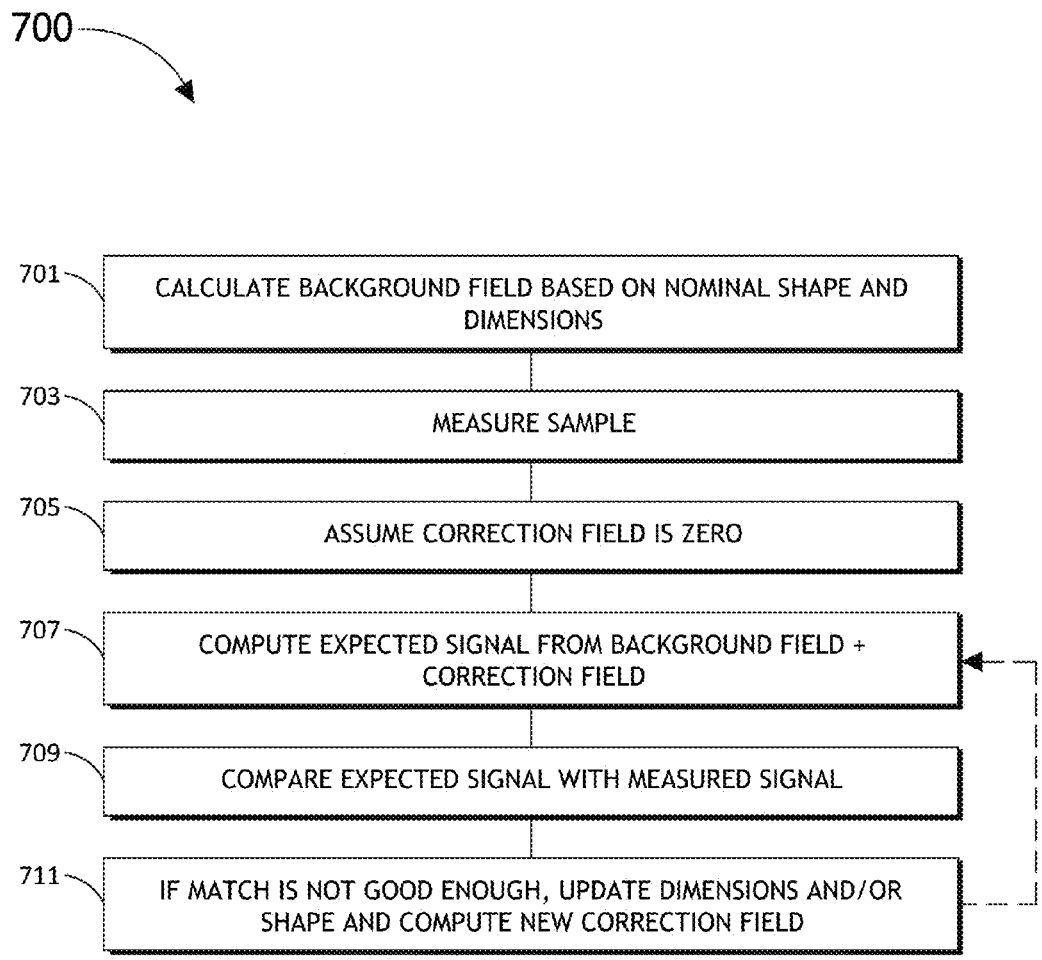
FIG. 7 is a flow diagram illustrating a real-time regression method used to determine one or more optical characteristics of a structure, in accordance with one embodiment of the present invention.

FIG. 7 illustrates a flow diagram for real-time regression method used to determine one or more optical characteristics of a structure, in accordance with one embodiment of the present invention. In step 701, a background field $E_B$ is calculated based on a set of nominal (or previously measured) shape and dimensions. In one aspect, the background field $E_B$ may be computed using any algorithm known in the art including, but not limited to, RCWA, Green's functions, FDTD or finite-element methods. In step 703, the sample is measured. In step 705, when a sample is measured, the correction field $E_C$ is initially assumed to be zero. In step 707, the expected signal is computed from the sum of the background field $E_B$ and correction field $E_C$. In step 709, the expected signal is compared with the measured signal. If the expected signal and measured signal match within a selected tolerance level, then the assumed shape and dimensions are deemed correct. If the match is not satisfactory, then at step 711, dimensions and/or the shape are modified and a new correction field is computed. The process 700 then repeats from step 707 until a satisfactory match is achieved. In one embodiment, a match may be deemed satisfactory when the expected and measured signals differ by an amount similar in magnitude to the expected system noise and system errors.

Figure 8:
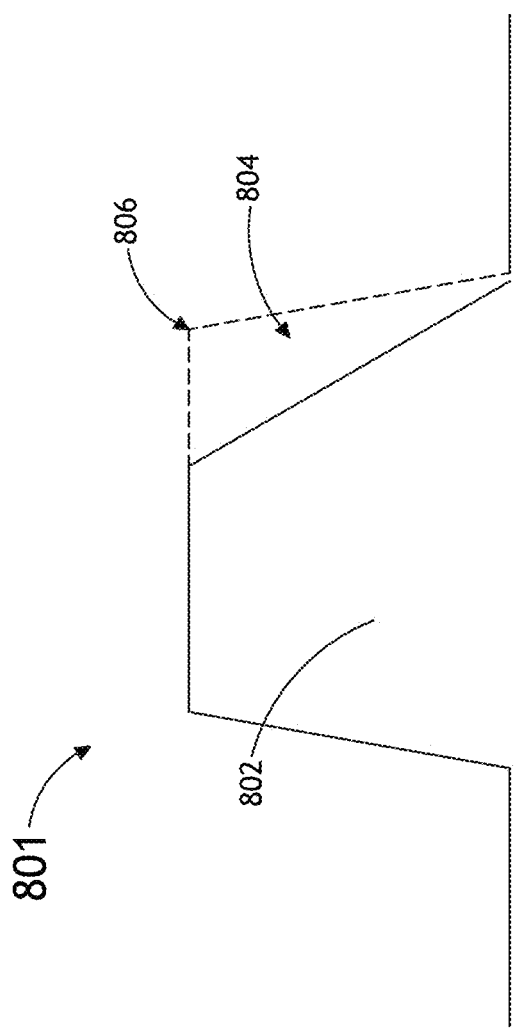
FIG. 8 is a schematic view of a unit cell of a repeating structure, in accordance with one embodiment of the present invention.

FIG. 8 illustrates a cross-sectional view of a unit cell 801 of a periodic structure on a surface 802, in accordance with one embodiment of the current invention. In another aspect, the profile of the unit cell structure 801 is not symmetric. It is noted that in some settings, calculation of the electric fields and reflectivity of a periodic structure is more efficient for symmetric structure than for structure that lack symmetry. In some embodiments of the present invention, the background field $E_B$ is calculated for a symmetric version of the structure 801 using an algorithm, such as RCWA. The difference between the symmetric structure and the asymmetric structure is then used to compute the correction field $E_C$. For example, as shown in FIG. 8, the structure 801 may be made symmetric by adding extra material(s) 804, which acts to make the right edge 806 the mirror image of the left edge as shown by the dotted line in FIG. 8. In an alternative embodiment, material could be removed from the left edge to make the left edge the mirror image of the right edge (not shown in FIG. 8). In another embodiment, both the left and right edges may be modified to generate a symmetric structure. In all of these cases, $E_C$ may be calculated based on the material 804 that is added or removed (in a virtual sense) in order to symmetrize the original structure 801. Again, although the above example illustrates a simple shape with a two-dimensional unit cell, it is to be understood that the present embodiment may be extended to a three-dimensional unit cell and to more complex shapes.

Figure 9:
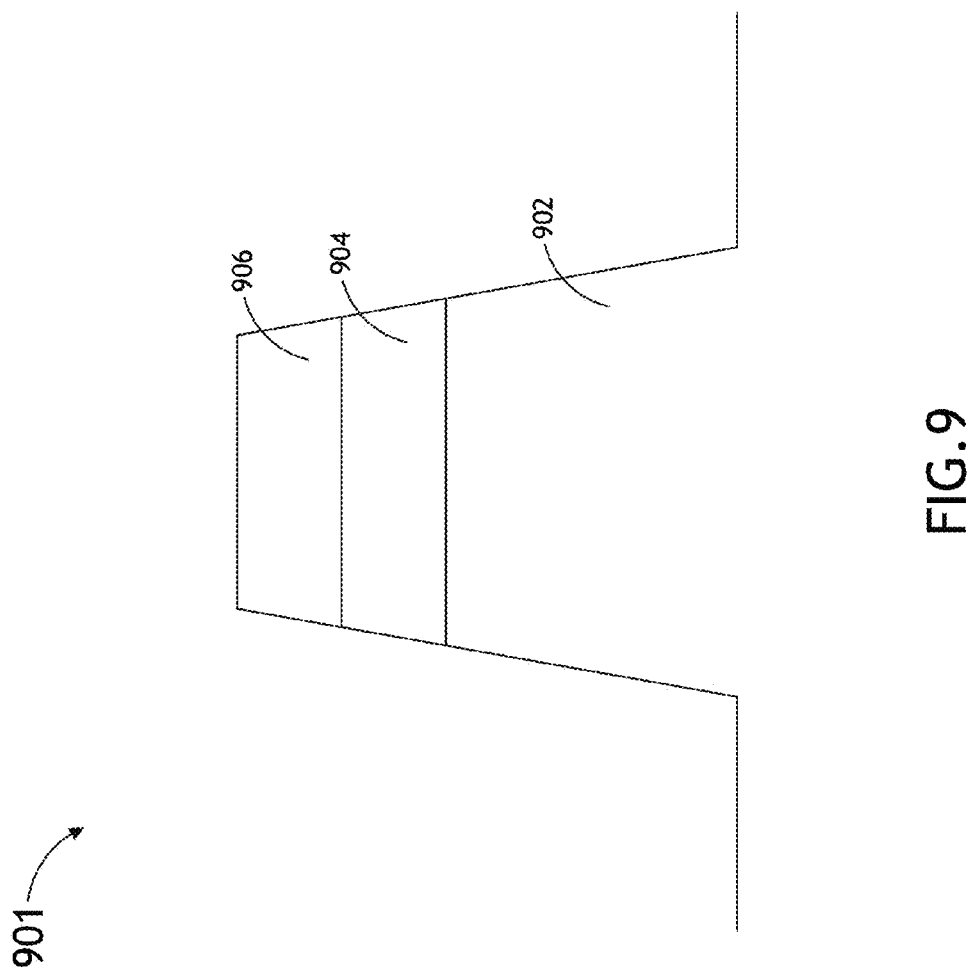
FIG. 9 is a schematic view of a unit cell of a multi-layered repeating structure, in accordance with one embodiment of the present invention.

FIG. 9 illustrates a cross-sectional view of a unit cell 901 of a multi-layered periodic structure, in accordance with one embodiment of the present invention. In one aspect, the periodic structure, shown as a cross section of a single unit cell 901, may include multiple materials such as, but not limited to, layer 902, 904 and 906. In a further aspect, if one of those layers, for example layer 904, is a magnetic material, a material with a high refractive index, or a material with strong absorption, computation of the electric fields may be substantially slower than for a similar structure where all materials are non-magnetic, and non-absorbing or weakly absorbing. In some embodiments of the present invention, the refractive index or relative permeability and permittivity of the magnetic or strongly absorbing material (such as, but not limited to, layer 904 in this example) may be set to values corresponding to weak or no absorption and a relative permeability of 1 for the calculation of $E_B$. Then, $E_C$ may be calculated based on the difference between the material constants used for calculating $E_B$ and the actual values of those material constants.

Figure 10:
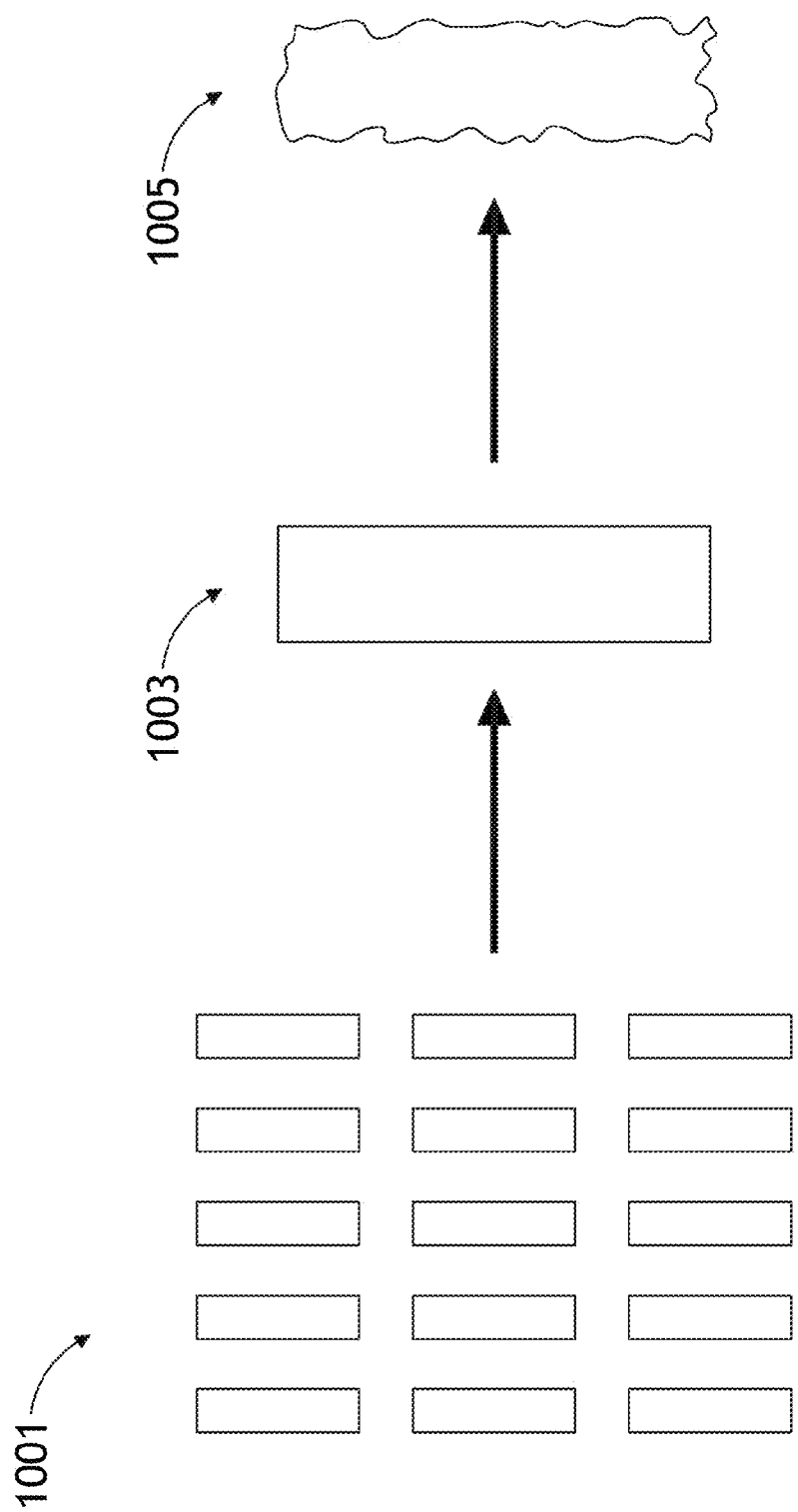
FIG. 10 is a top view of a periodic structure, an idealized unit cell of the periodic structure, and an estimation of a real unit cell, in accordance with one embodiment of the present invention.

FIG. 10 illustrates a top view of a periodic structure 1001, an idealized unit cell 1003 of the periodic structure, and an estimation of the real unit cell 1005 of the structure, in accordance with one embodiment of the present invention.

It is to be understood that the embodiment illustrated in FIG. 10 is equally applicable to structures that are periodic in one direction and constant in the perpendicular direction. It is further noted that, although the structure and unit cells are shown as rectangular, it is to be understood that provided shape is merely for illustrative purposes and the shapes may be more complex than depicted in FIG. 10. It is further noted that the vertical dimension is also not depicted in FIG. 10 and may take any simple or complex shape. It is recognized herein that in a real structure, each unit cell 1005 departs from its ideal shape 1003 due to roughness, including effects, such as line-edge roughness, line-width roughness and various other distortions, such as wiggles. Since these irregularities do not repeat exactly from unit cell to unit and, furthermore, they are typically much smaller than the unit cell, algorithms for calculating the fields and/or optical reflectivities of a periodic structure cannot include these irregularities in their calculation. In some embodiments of the present invention, $E_B$ is calculated for the periodic structure assuming all unit cells are identical (see idealized unit cells 1003). Then, $E_C$ may be calculated for the non-repeating portion of the real unit cells 1005 based on the extra and missing material around the surface of the real unit cells 1005. It is further noted herein that since the irregularities do not repeat, a larger unit cell may be needed or the calculation of $E_C$. In addition, since the irregularities typically become uncorrelated over long distances, it may suffice to take a unit cell for the calculation of $E_C$ that is only a few times the size of the unit cell of the ideal regular structure. Since the right hand side of Eq. 6 (or Eq. 5 as applicable) is zero nearly everywhere, the computation speed may still be acceptable.

Figure 11:
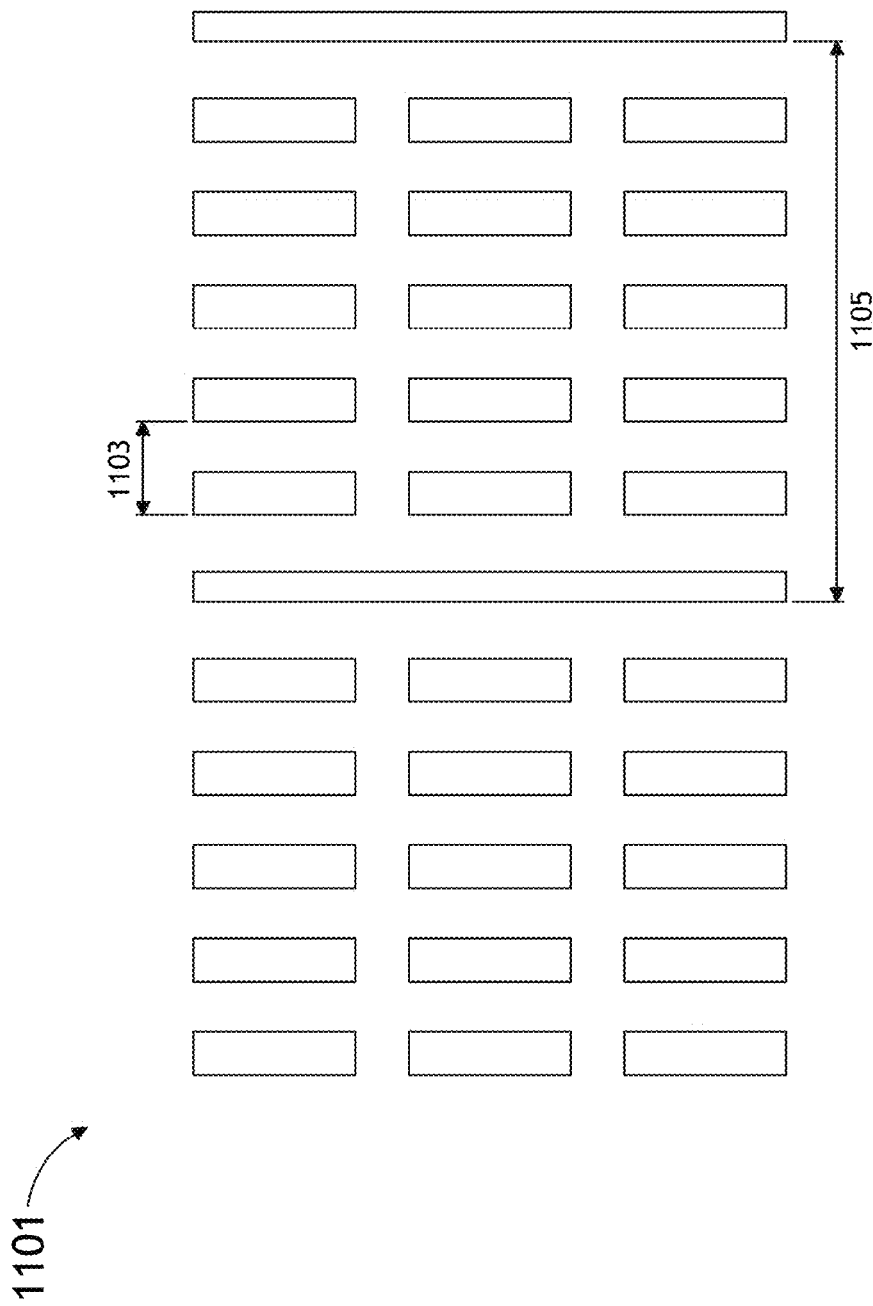
FIG. 11 is a top view of a periodic structure, in accordance with one embodiment of the present invention.

FIG. 11 illustrates a top view of a periodic structure 1101, in accordance with one embodiment of the present invention. In one embodiment, the periodic structure 1101 includes a large period 1105 in at least one direction, which includes a number of smaller structures that repeat on a smaller period 1103. An accurate calculation of the fields and/or reflectivities of the structure 1101 requires a calculation for the larger unit cell (with periodicity 1105), but with sufficient spatial resolution or truncation orders to fully capture the details of the small sub-features (with periodicity 1103). It is noted herein that the computation time for such a calculation may be prohibitive, even if the computer has sufficient memory to permit such a calculation. Ignoring the larger pitch and calculating the fields and/or reflectivities as if the smaller features repeat on pitch 1103 may approximate the correct fields and reflectivities under some conditions, but may be quite inaccurate under other conditions. In some embodiments of the present invention, $E_B$ is calculated for the smaller structure with pitch 1103 as if those smaller structures repeat indefinitely. Then, the correction field $E_C$ may be calculated for the difference between the true structure and the simplified structure.

Figure 12:
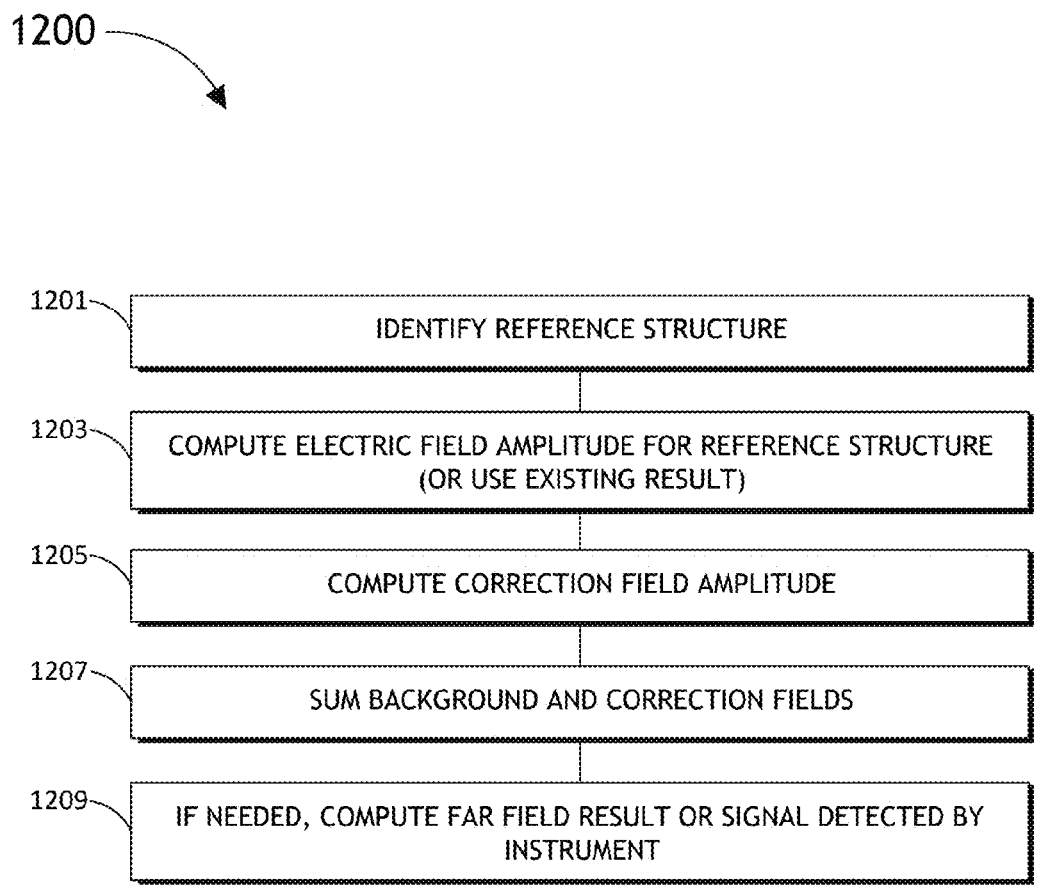
FIG. 12 is a flow diagram illustrating a determination one or more optical characteristics of a structure, in accordance with one embodiment of the present invention.

FIG. 12 illustrates a flow diagram depicting a method for determining one or more optical characteristics of a structure, in accordance with one embodiment of the present invention. In step 1201, reference structure is identified and/or constructed. In step 1203, the background electric fields $E_B$ are calculated for the identified and/or constructed reference structure. In an alternative embodiment, results of a prior calculation for the background structure may be retrieved. In some embodiments, the step 1203 may include calculating the fields for reference structure using one or more algorithms, such as, but not limited to, RCWA, Green's functions, FDTD, finite element methods (e.g., COMSOL Multiphysics (COMSOL AB, Stockholm, Sweden) or JCMsuite (JCMWave, Munich, Germany)). In step 1205, the correction field is calculated. For example, the correction field $E_C$ may be calculated by solving Eq. 6 (or Eq. 5 for magnetic materials), as described previously herein. In a further aspect, step 1205 may include calculating the correction field $E_C$ using a finite element method. In step 1207, a total field is generated by summing the background field $E_B$ and correction field $E_C$. In step 1209, if needed, the far field may be calculated or the generated total field may be compared to the detected field (e.g., detected by instrument).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

What is claimed:

1. A system for determining one or more optical characteristics of a structure, comprising:
   an optical measurement system including at least one light source for illuminating a portion of a sample with radiation, wherein the optical measurement system includes at least one detector configured to measure one or more optical signals from one or more structures of the sample;
   a computer control system, the computer control system including one or more processors communicatively coupled to the optical measurement system, the one or more processors configured to execute program instructions stored in memory and configured to cause the one or more processors to:
      receive one or more measured optical signals of the one or more structures from the optical measurement system;
      determine a background optical field associated with a symmetric reference structure having a selected set of nominal characteristics based on the one or more structures;
      determine a correction optical field suitable for at least partially correcting the background field, wherein a difference between the measured one or more optical signals and a signal associated with a sum of the correction optical field and the background optical field is below a selected tolerance level; and
      extract one or more characteristics associated with the one or more structures utilizing at least the correction optical field.

2. The system of claim 1, wherein the determining a correction optical field suitable for at least partially correcting the background field comprises:
   determining a correction optical field suitable for at least partially correcting the background field utilizing a finite element analysis procedure.

3. The system of claim 1, wherein the determining a background optical field associated with a symmetric reference structure having a selected set of nominal characteristics based on the one or more structures comprises:
   determining a background optical field associated with a symmetric reference structure having a selected set of nominal characteristics based on the one or more structures utilizing a finite element analysis procedure.

4. The system of claim 1, wherein the determining a background optical field associated with a symmetric reference structure having a selected set of nominal characteristics based on the one or more structures comprises:
determining a background optical field associated with a symmetric reference structure having a selected set of nominal characteristics based on the one or more structures utilizing at least one of a rigorous coupled-wave algorithm (RCWA), a Green's function method, and a finite-difference time domain method.

5. The system of claim 1, wherein the control system utilizes a finite element procedure having a first mesh to determine the background optical field and a second mesh to determine the correction optical field, wherein the first mesh and the second mesh are different.

6. The system of claim 1, wherein the control system utilizes a finite element procedure having a first set of boundary conditions to determine the background optical field and a second set of boundary conditions to determine the correction optical field, wherein the first set of boundary conditions and the second set of boundary conditions are different.

7. The system of claim 1, wherein the optical measurement system comprises:
an optical metrology system.

8. The system of claim 7, wherein the optical metrology system comprises:
at least one of a spectroscopic ellipsometer, a beam-profile reflectometer and a beam-profile ellipsometer.

9. The system of claim 1, wherein the optical measurement system comprises:
an optical inspection system.

10. The system of claim 9, wherein the optical inspection system comprises:
at least one of a dark-field inspection system and a bright-field inspection system.

11. The system of claim 1, wherein the extracted one or more characteristics comprise:
a defect characteristic.

12. The system of claim 1, wherein the extracted one or more characteristics comprise:
a dimensional characteristic.

13. The system of claim 1, wherein the extracted one or more characteristics comprise:
an optical characteristic.

14. The system of claim 13, wherein the optical characteristic comprises:
at least one of an optical reflectivity, optical scattering, and optical diffraction from the one or more structures.

15. The system of claim 1, wherein the extracting one or more characteristics associated with the one or more structures utilizing at least the correction optical field comprises:
extracting one or more characteristics associated with the one or more structures utilizing the correction optical field and the background optical field.

16. The system of claim 1, wherein the sample is a semiconductor wafer.

17. A method for determining one or more optical characteristics of a structure, comprising:
measuring one or more optical signals from one or more structures of a sample;
determining a background optical field associated with a symmetric reference structure having a selected set of nominal characteristics based on the one or more structures;
determining a correction optical field suitable for at least partially correcting the background field, wherein a difference between the measured one or more optical signals and a signal associated with a sum of the correction optical field and the background optical field is below a selected tolerance level; and
extracting one or more characteristics associated with the one or more structures utilizing the correction optical field.

18. The method of claim 17, wherein the determining a correction optical field suitable for at least partially correcting the background field comprises:
determining a correction optical field suitable for at least partially correcting the background field utilizing a finite element analysis procedure.

19. The method of claim 17, wherein the determining a background optical field associated with a symmetric reference structure having a selected set of nominal characteristics based on the one or more structures comprises:
determining a background optical field associated with a symmetric reference structure having a selected set of nominal characteristics based on the one or more structures utilizing a finite element analysis procedure.

20. The method of claim 17, wherein the determining a background optical field associated with a symmetric reference structure having a selected set of nominal characteristics based on the one or more structures comprises:
determining a background optical field associated with a symmetric reference structure having a selected set of nominal characteristics based on the one or more structures utilizing at least one of a rigorous coupled-wave algorithm (RCWA), a Green's function method, and a finite-difference time domain method.

21. The method of claim 17, wherein the background optical field is determined utilizing a finite element procedure having a first mesh and the correction optical field is determined utilizing a finite element procedure having a second mesh, wherein the first mesh and the second mesh are different.

22. The method of claim 17, wherein the background optical field is determined utilizing a finite element procedure having a first set of boundary conditions and the correction optical field is determined utilizing a finite element procedure having a second set of boundary conditions, wherein the first set of boundary conditions and the second set of boundary conditions are different.

23. The method of claim 17, wherein the extracted one or more characteristics comprise:
a defect characteristic.

24. The method of claim 17, wherein the extracted one or more characteristics comprise:
a dimensional characteristic.

25. The method of claim 17, wherein the extracted one or more characteristics comprise:
an optical characteristic.

26. The method of claim 17, wherein the optical characteristic comprises:
at least one of an optical reflectivity, optical scattering, and optical diffraction from the one or more structures.

27. A method for determining one or more optical characteristics of a structure, comprising:
determining a background optical field associated with a symmetric reference structure having a selected set of nominal characteristics based on the one or more structures;
measuring one or more optical signals from one or more structures of a sample;
determining a correction optical field suitable for at least partially correcting the background field;

determining an expected optical signal utilizing a sum of the background optical field and the correction optical field; and comparing the expected optical signal to the one or more measured optical signals in order to determine a level of convergence of the expected optical signal with respect to the one or more measured optical signals.

28. The method of claim 27, further comprising:

upon detecting a level of convergence below a selected tolerance level, extracting one or more characteristics associated with the one or more structures utilizing the correction optical field.

29. The method of claim 27, further comprising:

upon detecting a level of convergence above a selected tolerance level, determining an adjusted background optical field associated with an adjusted reference structure having a selected set of adjusted nominal characteristics based on the one or more structures;

measuring one or more optical signals from the one or more structures of the sample;

determining an adjusted correction optical field suitable for at least partially correcting the adjusted background field;

determining an adjusted expected optical signal utilizing a sum of the adjusted background optical field and the adjusted correction optical field;

comparing the adjusted expected optical signal to the one or more measured optical signals in order to determine an additional level of convergence of the adjusted expected optical signal with respect to the one or more measured optical signals; and upon detecting an adjusted level of convergence below a selected tolerance level, extracting one or more characteristics associated with the one or more structures utilizing the adjusted correction optical field.

* * * * *